(12) United States Patent
Scheller et al.

(10) Patent No.: US 9,629,645 B2
(45) Date of Patent: Apr. 25, 2017

(54) ATRAUMATIC MICROSURGICAL FORCEPS

(71) Applicant: Katalyst Surgical, LLC, Chesterfield, MO (US)

(72) Inventors: Gregg D Scheller, Wildwood, MO (US); Carl C Awh, Nashville, TN (US)

(73) Assignee: Katalyst Surgical, LLC, Chesterfield, MO (US)

( * ) Notice: Subject to any disclaimer, the term of this patent is extended or adjusted under 35 U.S.C. 154(b) by 452 days.

(21) Appl. No.: 14/029,721

(22) Filed: Sep. 17, 2013

(65) Prior Publication Data

US 2014/0121697 A1    May 1, 2014

Related U.S. Application Data

(60) Provisional application No. 61/720,290, filed on Oct. 30, 2012.

(51) Int. Cl.
| *A61B 17/00* | (2006.01) |
| *A61B 17/30* | (2006.01) |
| *A61F 9/007* | (2006.01) |
| *A61B 17/29* | (2006.01) |

(52) U.S. Cl.
CPC ...... *A61B 17/30* (2013.01); *A61B 2017/2918* (2013.01); *A61B 2017/2933* (2013.01); *A61B 2017/2937* (2013.01); *A61B 2017/305* (2013.01); *A61F 9/00736* (2013.01)

(58) Field of Classification Search
CPC .... A61F 9/0736; A61F 9/00736; A61B 17/28; A61B 17/29; A61B 17/282; A61B 17/30; A61B 17/2909; A61B 2017/2926; A61B 2017/2918; A61B 2017/305; A61B 2017/2933; B25B 9/02; A47G 21/103; A47G 21/10

USPC ................. 606/205–207; 294/99.2
See application file for complete search history.

(56) References Cited

U.S. PATENT DOCUMENTS

| 5,286,255 | A | * | 2/1994 | Weber ............... A61B 17/1608 |
| | | | | 600/565 |
| 5,318,589 | A | * | 6/1994 | Lichtman .......... A61B 18/1445 |
| | | | | 600/564 |
| 5,355,871 | A | | 10/1994 | Hurley et al. |
| 5,370,658 | A | | 12/1994 | Scheller et al. |
| 5,527,313 | A | | 6/1996 | Scott et al. |

(Continued)

OTHER PUBLICATIONS

Steve Charles, Techniques and tools for dissection of epiretinal membranes, Graefe' Arch Clin Exp Ophthalmol, 241:347-352, 2003.

*Primary Examiner* — Melanie Tyson
*Assistant Examiner* — Erich Herbermann
(74) *Attorney, Agent, or Firm* — Kevin P. Rollins

(57) ABSTRACT

An atraumatic microsurgical forceps may include a handle having a handle distal end and a handle proximal end, an outer hypodermic tube having an outer hypodermic tube distal end and an outer hypodermic tube proximal end, a surgical blank having a surgical blank distal end and a surgical blank proximal end, and a plurality of atraumatic forceps jaws of the surgical blank each atraumatic forceps jaw of the plurality of atraumatic forceps jaws having an atraumatic forceps jaw distal end and an atraumatic forceps jaw proximal end. A compression of the handle may be configured to gradually close the plurality of atraumatic forceps jaws wherein the plurality of atraumatic forceps jaws initially contact at the atraumatic forceps jaws distal ends.

20 Claims, 30 Drawing Sheets

(56) References Cited

U.S. PATENT DOCUMENTS

| | | |
|---|---|---|
| 5,810,811 A * | 9/1998 | Yates ............... A61B 17/07207 227/180.1 |
| 5,893,873 A | 4/1999 | Rader et al. |
| 5,893,877 A * | 4/1999 | Gampp, Jr. ........ A61B 17/2909 606/205 |
| 5,921,998 A | 7/1999 | Tano et al. |
| 6,159,162 A | 12/2000 | Kostylev et al. |
| 6,277,100 B1 | 8/2001 | Raulerson et al. |
| 6,488,695 B1 | 12/2002 | Hickingbotham |
| 6,575,989 B1 | 6/2003 | Scheller et al. |
| 6,730,076 B2 | 5/2004 | Hickingbotham |
| 6,863,668 B2 | 3/2005 | Gillespie et al. |
| 6,908,476 B2 * | 6/2005 | Jud ............... A61B 17/320016 606/107 |
| 7,632,242 B2 | 12/2009 | Griffin et al. |
| 7,731,728 B2 * | 6/2010 | Glaser ................ A61F 9/00736 606/161 |
| 7,766,904 B2 | 8/2010 | Mc Gowan, Sr. et al. |
| 8,038,692 B2 | 10/2011 | Valencia et al. |
| 8,197,468 B2 | 6/2012 | Scheller et al. |
| 2003/0171762 A1 | 9/2003 | Forchette et al. |
| 2005/0154403 A1 | 7/2005 | Sauer et al. |
| 2006/0235382 A1 | 10/2006 | Cohen et al. |
| 2007/0185514 A1 | 8/2007 | Kirchhevel |
| 2007/0282348 A1 | 12/2007 | Lumpkin |
| 2008/0183199 A1 | 7/2008 | Attinger |
| 2009/0228066 A1 | 9/2009 | Hirata et al. |
| 2010/0023050 A1 * | 1/2010 | Reinauer ................ A61B 17/29 606/207 |
| 2012/0116361 A1 | 5/2012 | Hanlon et al. |
| 2012/0150216 A1 | 6/2012 | Hickingbotham et al. |
| 2012/0191120 A1 | 7/2012 | Linsi |
| 2013/0085326 A1 | 4/2013 | Scheller et al. |
| 2013/0197488 A1 | 8/2013 | Scheller et al. |
| 2014/0066977 A1 | 3/2014 | Scheller et al. |
| 2014/0121697 A1 | 5/2014 | Scheller et al. |
| 2014/0128909 A1 | 5/2014 | Scheller et al. |
| 2014/0142603 A1 | 5/2014 | Scheller et al. |
| 2014/0172010 A1 | 6/2014 | Vezzu |
| 2014/0277110 A1 | 9/2014 | Scheller et al. |
| 2015/0088193 A1 | 3/2015 | Scheller et al. |

* cited by examiner

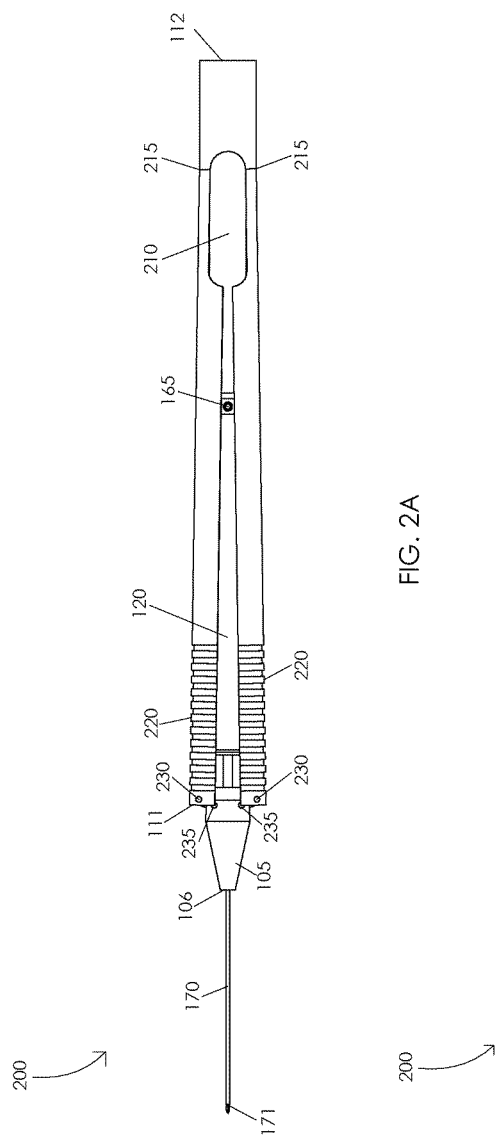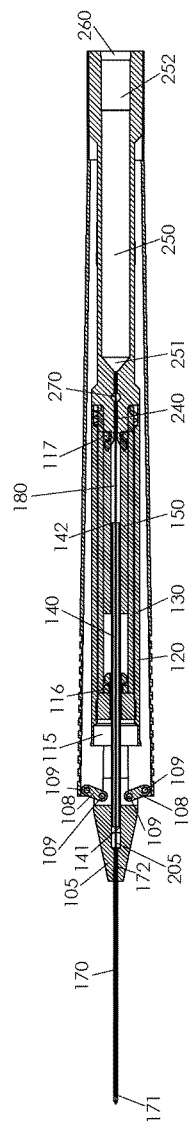
FIG. 2A
FIG. 2B

TOP                FRONT

TOP   FRONT

TOP

FRONT

ATRAUMATIC MICROSURGICAL FORCEPS

CROSS-REFERENCE TO RELATED APPLICATIONS

This application claims the benefit of U.S. Provisional Application No. 61/720,290, filed Oct. 30, 2012.

FIELD OF THE INVENTION

The present disclosure relates to a surgical instrument, and, more particularly, to a microsurgical forceps.

BACKGROUND OF THE INVENTION

A microsurgical forceps may be used to perform a microsurgical procedure, e.g., an ophthalmic surgical procedure. For example, a surgeon may use a forceps to grasp and manipulate tissues or other surgical instruments to perform portions of a surgical procedure. A particular microsurgical procedure may require a surgeon to separate a first tissue from a second tissue without causing trauma to at least one of the tissues. Such a separation procedure may be particularly difficult for a surgeon to perform if the tissue surface geometry is not flat, e.g., if the tissue surface geometry is convex. For example, an ophthalmic surgeon may be required to remove an internal limiting membrane from a patient's retina without causing trauma to the patient's retina. Accordingly, there is a need for a microsurgical forceps that enables a surgeon to separate a first tissue from a second tissue without causing trauma to at least one of the tissues.

BRIEF SUMMARY OF THE INVENTION

The present disclosure presents an atraumatic microsurgical forceps. Illustratively, an atraumatic microsurgical forceps may comprise a handle having a handle distal end and a handle proximal end, an outer hypodermic tube having an outer hypodermic tube distal end and an outer hypodermic tube proximal end, a surgical blank having a surgical blank distal end and a surgical blank proximal end, and a plurality of atraumatic forceps jaws of the surgical blank each atraumatic forceps jaw of the plurality of atraumatic forceps jaws having an atraumatic forceps jaw distal end and an atraumatic forceps jaw proximal end. In one or more embodiments, the surgical blank may be disposed in the handle and the outer hypodermic tube wherein at least a portion of the plurality of atraumatic forceps jaws extends from the outer hypodermic tube distal end. Illustratively, a compression of the handle may be configured to extend the outer hypodermic tube relative to the plurality of atraumatic forceps jaws. In one or more embodiments, an extension of the outer hypodermic tube relative to the plurality of atraumatic forceps jaws may be configured to gradually close the plurality of atraumatic forceps jaws wherein the plurality of atraumatic forceps jaws initially contact at the atraumatic forceps jaws distal ends.

BRIEF DESCRIPTION OF THE DRAWINGS

The above and further advantages of the present invention may be better understood by referring to the following description in conjunction with the accompanying drawings in which like reference numerals indicate identical or functionally similar elements:

FIGS. 2A and 2B are schematic diagrams illustrating an assembled surgical instrument;

DETAILED DESCRIPTION OF AN ILLUSTRATIVE EMBODIMENT

Figure 1:
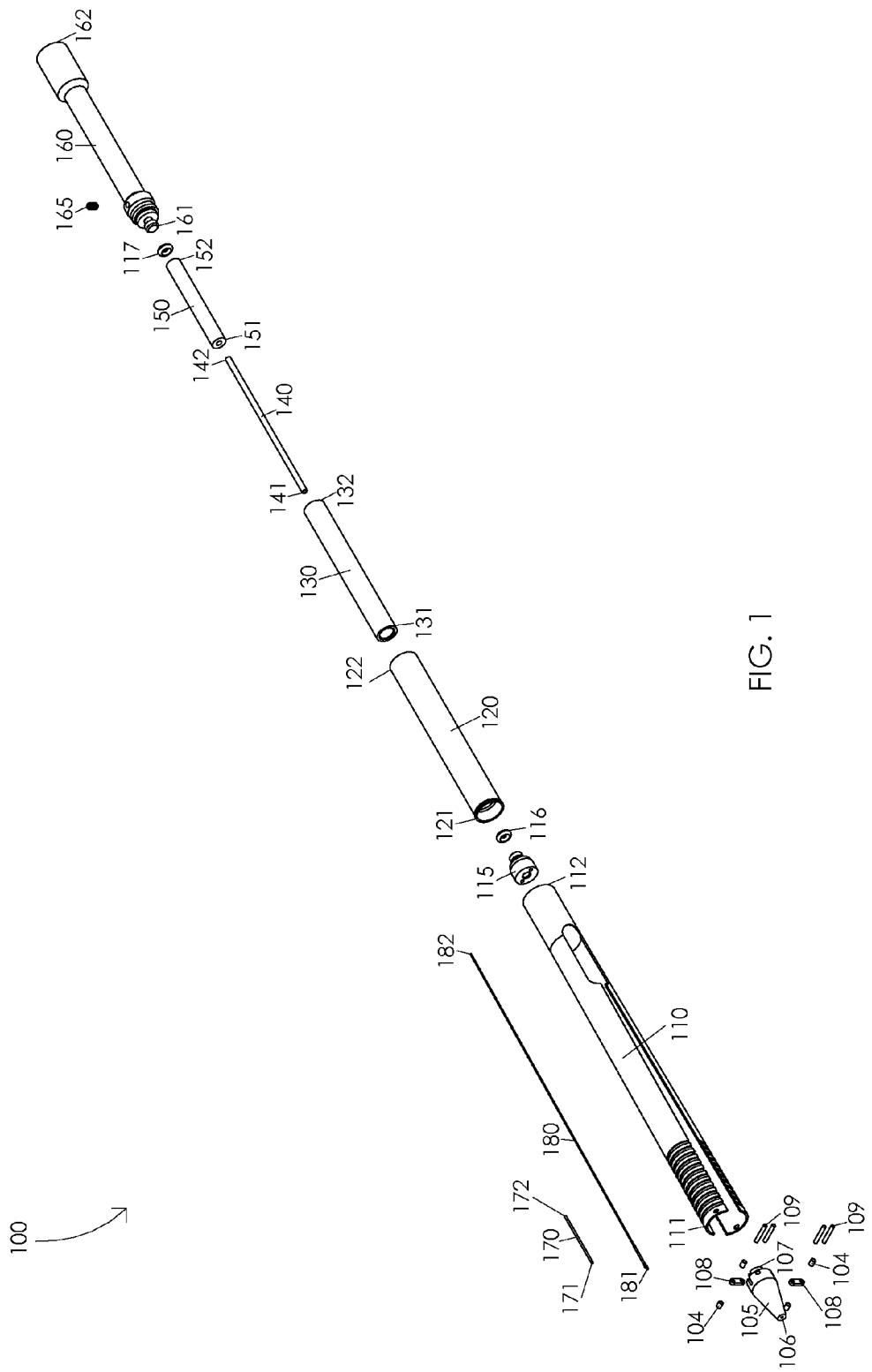
FIG. 1 is a schematic diagram illustrating an exploded view of a surgical instrument assembly.

FIG. 1 is a schematic diagram illustrating an exploded view of a surgical instrument assembly 100. In one or more embodiments, surgical instrument assembly 100 may comprise a nosecone 105 having a nosecone distal end 106 and a nosecone proximal end 107; one or more links 108; one or more link pins 109; one or more spacers 104; a handle 110 having a handle distal end 111 and a handle proximal end 112; a front plug 115; a distal O-ring 116; a proximal O-ring 117; a housing sleeve 120 having a housing sleeve distal end 121 and a housing sleeve proximal end 122; an actuation facilitating sleeve 130 having an actuation facilitating sleeve distal end 131 and an actuation facilitating sleeve proximal end 132; an inner hypodermic tube 140 having an inner hypodermic tube distal end 141 and an inner hypodermic tube proximal end 142; a piston tube 150 having a piston tube distal end 151 and a piston tube proximal end 152; an end plug 160 having an end plug distal end 161 and an end plug proximal end 162; a fixation mechanism 165; an outer hypodermic tube 170 having an outer hypodermic tube distal end 171 and an outer hypodermic tube proximal end 172; and a surgical blank 180 having a surgical blank distal end 181 and a surgical blank proximal end 182.

Illustratively, outer hypodermic tube 170 may be fixed to nosecone 105, e.g., outer hypodermic tube proximal end 172 may be fixed to nosecone distal end 106. In one or more embodiments, one or more links 108 and one or more link pins 109 may be configured to connect nosecone 105 and handle 110, e.g., a portion of nosecone 105 may be disposed within handle 110. Illustratively, nosecone 105 may be connected to one or more links 108, e.g., one or more link pins 109 may be disposed within both nosecone 105 and one or more links 108. In one or more embodiments, handle 110 may be connected to one or more links 108, e.g., one or more link pins 109 may be disposed within both handle 110 and one or more links 108. Illustratively, at least one link 108 may be connected to both nosecone 105 and handle 110, e.g., by one or more link pins 109.

In one or more embodiments, inner hypodermic tube 140 may be at least partially disposed within piston tube 150, e.g., inner hypodermic tube proximal end 142 may be disposed within piston tube 150. Illustratively, inner hypodermic tube 140 and piston tube 150 may be at least partially disposed within actuation facilitating sleeve 130. In one or more embodiments, actuation facilitating sleeve 130 and piston tube 150 may be disposed within housing sleeve 120. Illustratively, inner hypodermic tube 140 may be at least partially disposed within housing sleeve 120, e.g., inner hypodermic tube distal end 141 may extend a distance from housing sleeve distal end 121.

In one or more embodiments, distal O-ring 116 may be disposed over a portion of front plug 115. Illustratively, distal O-ring 116 may be disposed within housing sleeve 120 and actuation facilitating sleeve 130. In one or more embodiments, at least a portion of front plug 115 may be disposed within housing sleeve 120 and actuation facilitating sleeve 130, e.g., housing sleeve distal end 121 and actuation facilitating sleeve distal end 131 may be disposed over a portion of front plug 115. Illustratively, proximal O-ring 117 may be disposed over a portion of end plug 160. In one or more embodiments, proximal O-ring 117 may be disposed within housing sleeve 120 and actuation facilitating sleeve 130. Illustratively, at least a portion of end plug 160 may be disposed within housing sleeve 120 and actuation facilitating sleeve 130, e.g., housing sleeve proximal end 122 and actuation facilitating sleeve proximal end 132 may be disposed over a portion of end plug 160.

In one or more embodiments, front plug 115, distal O-ring 116, housing sleeve 120, actuation facilitating sleeve 130, piston tube 150, inner hypodermic tube 140, proximal O-ring 117, and end plug 160 may be disposed within handle 110. For example, end plug 160 may be disposed within handle 110 wherein end plug proximal end 162 may be adjacent to handle proximal end 112. Illustratively, inner hypodermic tube 140 may be fixed to nosecone 105, e.g., inner hypodermic tube distal end 141 may be fixed to nosecone proximal end 107.

In one or more embodiments, surgical blank 180 may be disposed within outer hypodermic tube 170, nosecone 105, inner hypodermic tube 140, piston tube 150, and end plug 160. Illustratively, fixation mechanism 165 may be configured to fix surgical blank 180 in a position relative to handle 110. For example, fixation mechanism 165 may comprise a setscrew configured to fix surgical blank 180 in a position relative to handle 110. In one or more embodiments, fixation mechanism 165 may comprise an adhesive material configured to fix surgical blank 180 in a position relative to handle 110. Illustratively, fixation mechanism 165 may comprise any suitable means of fixing surgical blank 180 in a position relative to handle 110.

FIGS. 2A and 2B are schematic diagrams illustrating an assembled surgical instrument 200. FIG. 2A illustrates a side view of an assembled surgical instrument 200. In one or more embodiments, housing sleeve 120 may be disposed within handle 110. Illustratively, actuation facilitating sleeve 130 may be disposed within housing sleeve 120. In one or more embodiments, piston tube 150 may be disposed within actuation facilitating sleeve 130. Illustratively, a portion of inner hypodermic tube 140 may be disposed within piston tube 150, e.g., inner hypodermic tube proximal end 142 may be disposed within piston tube 150. In one or more embodiments, a portion of inner hypodermic tube 140 may be fixed to an inner portion of piston tube 150, e.g., by a biocompatible adhesive. For example, an actuation of inner hypodermic tube 140 relative to handle 110 may be configured to actuate piston tube 150 relative to handle 110 and an actuation of piston tube 150 relative to handle 110 may be configured to actuate inner hypodermic tube 140 relative to handle 110.

Illustratively, handle 110 may comprise a spring return aperture 210. In one or more embodiments, spring return aperture 210 may comprise one or more hinges 215. Illustratively, spring return aperture 210 may be configured to separate a first portion of handle 110 and a second portion of handle 110. In one or more embodiments, spring return aperture 210 may be configured to separate a particular point on the first portion of handle 110 from a particular point on the second portion of handle 110 at a first distance. Illustratively, an application of a compressive force to a portion of handle 110 may be configured to separate the particular point on the first portion of handle 110 from the particular point on the second portion of handle 110 at a second distance. In one or more embodiments, the first distance may be greater than the second distance.

Illustratively, handle 110 may comprise one or more surgical grip points 220. In one or more embodiments, one or more surgical grip points 220 may be configured to prevent undesirable movements of handle 110, e.g., during a surgical procedure. Illustratively, one or more surgical grip points 220 may be configured to interface with a surgeon's fingertips. In one or more embodiments, one or more surgical grip points 220 may be configured to increase a total contact area between a surgeon's fingertips and handle 110. Illustratively, one or more surgical grip points 220 may be configured to facilitate an application of a compressive force to handle 110, e.g., by increasing a coefficient of friction between a surgeon's fingertips and handle 110 as the surgeon applies a compressive force to handle 110. Handle 110 may be manufactured from any suitable material, e.g., polymers, metals, metal alloys, etc., or from any combination of suitable materials.

In one or more embodiments, handle 110 may comprise one or more handle link pin housings 230. Illustratively, handle link pin housing 230 may be configured to house link pin 109. In one or more embodiments, nosecone 105 may comprise one or more nosecone link pin housings 235. Illustratively, nosecone link pin housing 235 may be configured to house link pin 109. In one or more embodiments, at least one link pin 109 may be configured to connect nosecone 105 to link 108, e.g., link pin 109 may be disposed within both nosecone link pin housing 235 and link 108. Illustratively, at least one link pin 109 may be configured to connect handle 110 and link 108, e.g., link pin 109 may be disposed within both handle link pin housing 230 and link 108. In one or more embodiments, at least one link 108 may be connected to both nosecone 105 and handle 110, e.g., at least one link pin 109 may be disposed within both nosecone link pin housing 235 and link 108 and at least one link pin 109 may be disposed within both handle link pin housing 230 and link 108.

FIG. 2B illustrates a cross-sectional view of an assembled surgical instrument 200. In one or more embodiments, nosecone 105 may comprise a nosecone inner bore 205. Illustratively, inner hypodermic tube distal end 141 may be fixed within nosecone inner bore 205, e.g., by a machine press fit, a biocompatible adhesive, etc. In one or more embodiments, outer nosecone proximal end 172 may be fixed within nosecone inner bore 205, e.g., by a machine press fit, a biocompatible adhesive, etc.

Illustratively, end plug 160 may comprise a surgical blank housing 240, an end plug inner bore 250, an interface taper 260, and a fixation mechanism housing 270. In one or more embodiments, end plug inner bore 250 may comprise an end plug inner bore distal cone 251 and an end plug inner bore proximal chamber 252. Illustratively, interface taper 260 may be configured to interface with one or more components, e.g., to provide one or more surgical utilities. In one or more embodiments, interface taper 260 may comprise a Luer taper. End plug 160 may be manufactured from any suitable material, e.g., polymers, metals, metal alloys, etc., or from any combination of suitable materials.

Illustratively, surgical blank 180 may be disposed within outer hypodermic tube 170, nosecone inner bore 205, inner hypodermic tube 140, piston tube 150, actuation facilitating sleeve 130, surgical blank housing 240, and fixation mechanism housing 270. In one or more embodiments, fixation mechanism 165 may be configured to fix surgical blank 180 in a position relative to handle 110, e.g., at fixation mechanism housing 270. For example, fixation mechanism 165 may be disposed within fixation mechanism housing 270, e.g., to fix surgical blank 180 in a position relative to handle 110.

Illustratively, surgical blank 180 may modified to provide a one or more surgical utilities, e.g., surgical blank distal end 181 may be modified to provide one or more particular surgical utilities of a plurality of surgical utilities. In one or more embodiments, surgical blank 180 may be modified wherein surgical blank 180 may comprise a surgical forceps, e.g., with a grasping utility. Illustratively, surgical blank 180 may be modified wherein surgical blank 180 may comprise a surgical scissors, e.g., with a cutting utility. In one or more embodiments, surgical blank 180 may be modified wherein surgical blank 180 may comprise a surgical manipulator, e.g., with a manipulation utility. Illustratively, surgical blank 180 may be modified wherein surgical blank 180 may comprise a surgical hook, e.g., with a hook utility. In one or more embodiments, surgical blank 180 may be modified wherein surgical blank 180 may comprise a surgical chopper, e.g. with a chopping utility. Illustratively, surgical blank 180 may be modified wherein surgical blank 180 may comprise a surgical pre-chopper, e.g., with a pre-chopping utility. In one or more embodiments, surgical blank 180 may be modified wherein surgical blank 180 may comprise a surgical pick, e.g., with a pick utility. Illustratively, surgical blank 180 may be modified to comprise any surgical instrument with any surgical utility as will be appreciated by one having ordinary skill in the relevant technological art. Surgical blank 180 may be manufactured from any suitable material, e.g., polymers, metals, metal alloys, etc., or from any combination of suitable materials.

In one or more embodiments, handle 110 may be compressed, e.g., by an application of a compressive force to handle 110. For example, a surgeon may compress handle 110 by gently squeezing handle 110, e.g., at one or more surgical grip points 220. Illustratively, a compression of handle 110 may be configured to actuate nosecone 105 relative to handle proximal end 112. Illustratively, a compression of handle 110 may be configured to extend nosecone 105 relative to handle proximal end 112.

In one or more embodiments, a compression of handle 110 may be configured to extend one or more links 108 connected to nosecone 105, e.g., by one or more link pins 109, away from handle proximal end 112. Illustratively, a compression of handle 110 may be configured to gradually project nosecone 105 relative to handle proximal end 112. In one or more embodiments, a compression of handle 110 may be configured to gradually actuate outer hypodermic tube 170 relative to handle proximal end 112. For example, a compression of handle 110 may be configured to gradually extend outer hypodermic tube 170 relative to handle proximal end 112. Illustratively, a compression of handle 110 may be configured to gradually actuate outer hypodermic tube 170 relative to surgical blank 180. For example, a compression of handle 110 may be configured to gradually extend outer hypodermic tube 170 relative to surgical blank 180.

In one or more embodiments, a compression of handle 110 may be configured to actuate inner hypodermic tube 140 relative to handle 110. Illustratively, a compression of handle 110 may be configured to extend inner hypodermic tube 140 relative to handle proximal end 112. In one or more embodiments, a compression of handle 110 may be configured to actuate piston tube 150 relative to handle 110. Illustratively, a compression of handle 110 may be configured to extend piston tube 150 relative to handle proximal end 112.

In one or more embodiments, handle 110 may be decompressed, e.g., by reducing a magnitude of a compressive force applied to handle 110. For example, a surgeon may decompress handle 110 by decreasing an amount of compressive force applied to handle 110, e.g., at one or more surgical grip points 220. Illustratively, a decompression of handle 110 may be configured to actuate nosecone 105 relative to handle proximal end 112. Illustratively, a decompression of handle 110 may be configured to retract nosecone 105 relative to handle proximal end 112.

In one or more embodiments, a decompression of handle 110 may be configured to retract one or more links 108 connected to nosecone 105, e.g., by one or more link pins 109, towards handle proximal end 112. Illustratively, a decompression of handle 110 may be configured to gradually retract nosecone 105 relative to handle proximal end 112. In one or more embodiments, a decompression of handle 110 may be configured to gradually actuate outer hypodermic tube 170 relative to handle proximal end 112. For example, a decompression of handle 110 may be configured to gradually retract outer hypodermic tube 170 relative to handle proximal end 112. Illustratively, a decompression of handle 110 may be configured to gradually actuate outer hypodermic tube 170 relative to surgical blank 180. For example, a decompression of handle 110 may be configured to gradually retract outer hypodermic tube 170 relative to surgical blank 180.

In one or more embodiments, a decompression of handle 110 may be configured to actuate inner hypodermic tube 140 relative to handle 110. Illustratively, a decompression of handle 110 may be configured to retract inner hypodermic tube 140 relative to handle proximal end 112. In one or more embodiments, a decompression of handle 110 may be configured to actuate piston tube 150 relative to handle 110. Illustratively, a decompression of handle 110 may be configured to retract piston tube 150 relative to handle proximal end 112.

In one or more embodiments, actuation facilitating sleeve 130 and piston tube 150 may be configured to minimize a coefficient of friction between actuation facilitating sleeve 130 and piston tube 150. Illustratively, actuation facilitating sleeve 130 and piston tube 150 may be manufactured from one or more materials configured to minimize a friction force, e.g., when piston tube 150 is actuated relative to handle 110. For example, actuation facilitation sleeve 130 and piston tube 150 may be manufactured from one or more materials configured to minimize a friction force, e.g., when piston tube 150 is actuated relative to actuation facilitating sleeve 130. In one or more embodiments, at least an inner portion of actuation facilitating sleeve 130 may comprise a non-crystalline material, e.g., glass. Illustratively, at least an outer portion of piston tube 150 may comprise carbon or a carbon allotrope, e.g., graphite. In one or more embodiments, at least an inner portion of actuation facilitating sleeve 130 may comprise a carbon or a carbon allots trope, e.g., graphite. Illustratively, at least an outer portion of piston tube 150 may comprise a non-crystalline material, e.g., glass.

Actuation facilitating sleeve 130 may be manufactured from any suitable material, e.g., polymers, metals, metal alloys, etc., or from any combination of suitable materials. Piston tube 150 may be manufactured from any suitable material, e.g., polymers, metals, metal alloys, etc., or from any combination of suitable materials. In one or more embodiments, an inner portion of actuation facilitating sleeve 130 may be coated with a material configured to minimize a coefficient of friction between actuation facilitating sleeve 130 and piston tube 150, e.g., Teflon. Illustratively, an outer portion of piston tube 150 may be coated with a material configured to minimize a coefficient of friction between piston tube 150 and actuation facilitation sleeve 130, e.g., Teflon.

Figure 3:
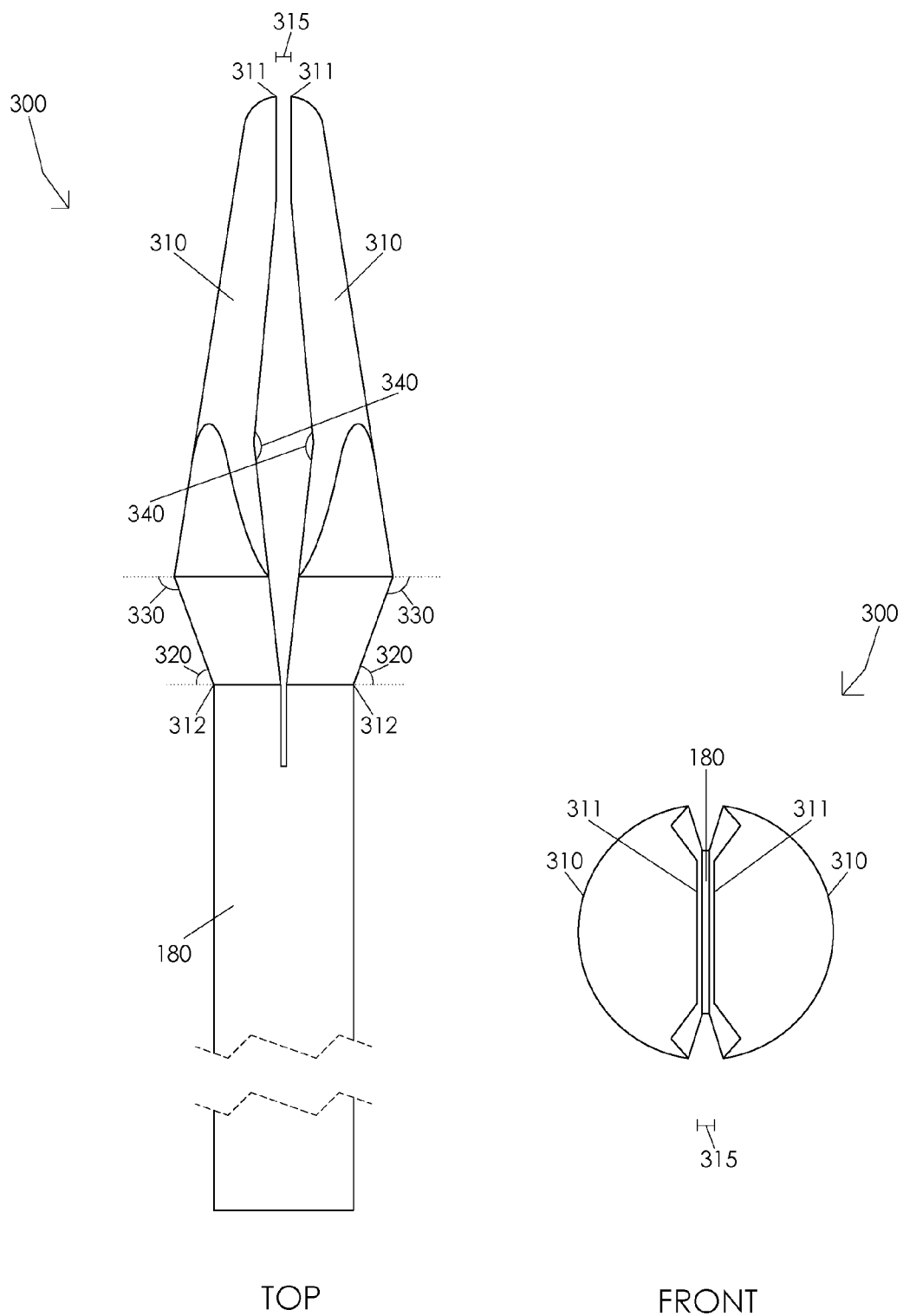
FIG. 3 is a schematic diagram illustrating an atraumatic forceps.

FIG. 3 is a schematic diagram illustrating an atraumatic forceps 300. FIG. 3 illustrates a top view and a front view of an atraumatic forceps 300. Illustratively, atraumatic forceps 300 may be manufactured with dimensions configured for performing microsurgical procedures, e.g., ophthalmic surgical procedures. In one or more embodiments, atraumatic forceps 300 may be manufactured from surgical blank 180. Illustratively, atraumatic forceps 300 may be manufactured by modifying surgical blank 180, e.g., with an electric discharge machine. In one or more embodiments, atraumatic forceps 300 may be manufactured by modifying surgical blank 180, e.g., with a laser, a file, or any suitable modification means. Illustratively, atraumatic forceps 300 may comprise a plurality of atraumatic forceps jaws 310, a first contour angle 320, a second contour angle 330, and a third contour angle 340.

Illustratively, each atraumatic forceps jaw 310 of a plurality of atraumatic forceps jaws 310 may comprise an atraumatic forceps jaw distal end 311 and an atraumatic forceps jaw proximal end 312. In one or more embodiments, a first atraumatic forceps jaw distal end 311 and a second atraumatic forceps jaw distal end 311 may be separated by a distance 315. Illustratively, distance 315 may comprise a distance in a range of 0.005 to 0.08 inches, e.g., distance 315 may comprise a distance of 0.04 inches. In one or more embodiments, distance 315 may comprise a distance less than 0.005 inches or greater than 0.08 inches. Illustratively, atraumatic forceps 300 may be configured to separate a first tissue from a surface of a second tissue without damaging the second tissue. For example, atraumatic forceps 300 may be configured to separate a first tissue having a convex surface geometry from a second tissue having a convex surface geometry without damaging the second tissue. In one or more embodiments, the first tissue may comprise an internal limiting membrane and the second tissue may comprise a retina. Illustratively, distance 315 may comprise a distance in a range of 200 to 600 times an average thickness of the first tissue, e.g., distance 315 may comprise a distance 291 times the average thickness of the first tissue. In one or more embodiments, distance 315 may comprise a distance less than 200 times or greater than 600 times the average thickness of the first tissue. Illustratively, distance 315 may comprise a distance in a range of 200 to 600 times an average thickness of an internal limiting membrane, e.g., distance 315 may comprise a distance 291 times the average thickness of an internal limiting membrane. In one or more embodiments, distance 315 may comprise a distance less than 200 times or greater than 600 times the average thickness of an internal limiting membrane.

Illustratively, first contour angle 320 may comprise any angle less than 90 degrees, e.g., first contour angle 320 may comprise an angle in a range of 60 to 80 degrees. In one or more embodiments, first contour angle 320 may comprise an angle less than 60 degrees or greater than 80 degrees. Illustratively, first contour angle 320 may comprise a 70 degree angle. In one or more embodiments, second contour angle 330 may comprise any angle greater than 90 degrees, e.g., second contour angle 330 may comprise an angle in a range of 100 to 120 degrees. Illustratively, second contour angle 330 may comprise an angle less than 100 degrees or greater than 120 degrees. In one or more embodiments, second contour angle 330 may comprise a 110 degree angle. Illustratively, third contour angle 340 may comprise any angle greater than 90 degrees, e.g., third contour angle 340 may comprise an angle in a range of 160 to 175 degrees. In one or more embodiments, third contour angle 340 may comprise an angle less than 160 degrees or greater than 175 degrees. Illustratively, third contour angle 340 may comprise a 168 degree angle.

In one or more embodiments, atraumatic forceps jaws 310 may be configured to close at atraumatic forceps jaws distal ends 311 as outer hypodermic tube 170 is gradually actuated over atraumatic forceps jaws proximal ends 312. Illustratively, an extension of outer hypodermic tube 170 relative to surgical blank 180 may be configured to decrease a distance 315 between a first atraumatic forceps jaw distal end 311 and a second atraumatic forceps jaw distal end 311. In one or more embodiments, an extension of outer hypodermic tube 170 over a first atraumatic forceps jaw proximal end 312 and a second atraumatic forceps jaw proximal end 312 may be configured to cause the first atraumatic forceps jaw distal end 311 and the second atraumatic forceps jaw distal end 311 to contact before any other portion of the first atraumatic forceps jaw 310 contacts any other portion of the second atraumatic forceps jaw 310.

Figure 4A:
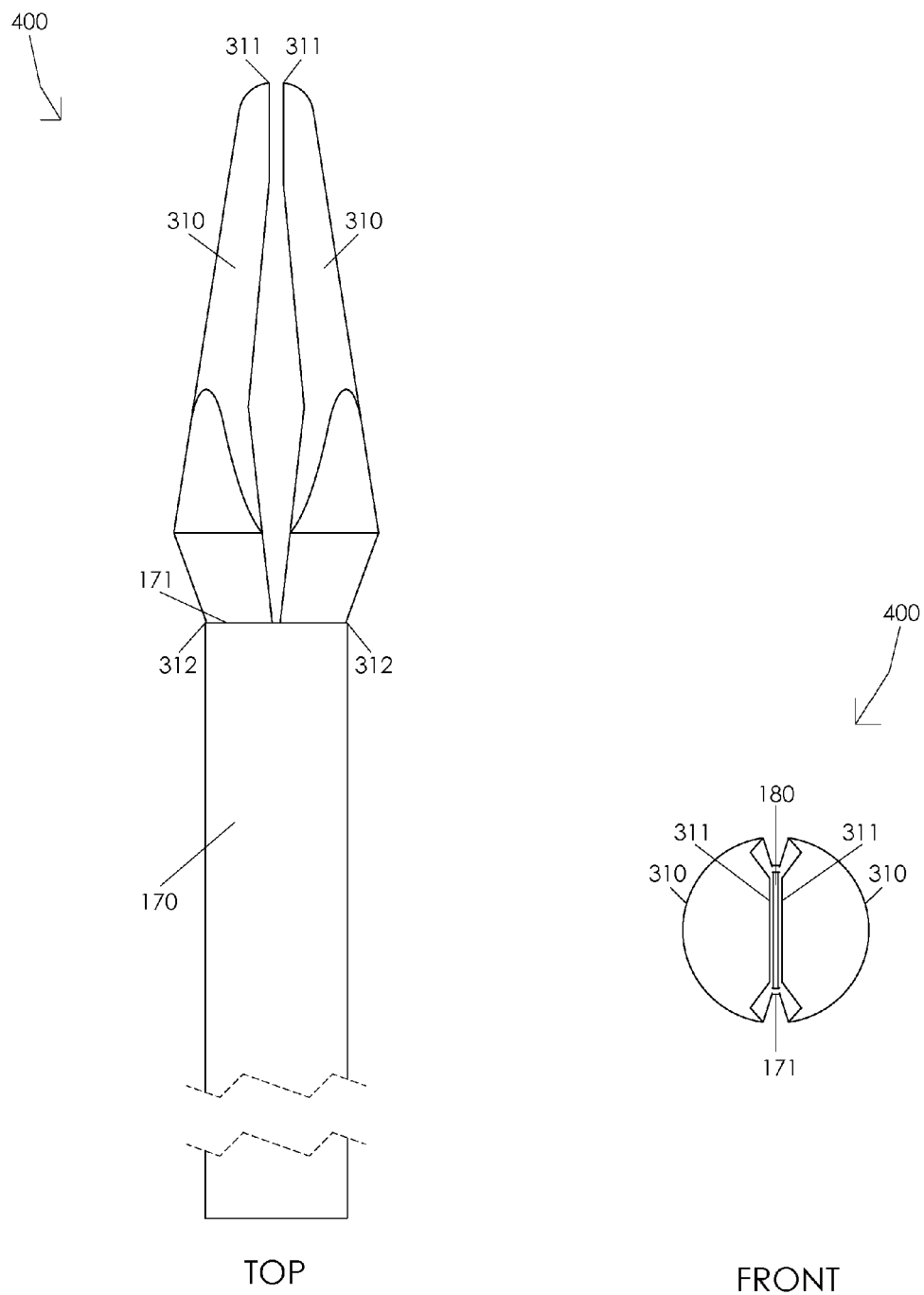
FIGS. 4A, 4B, and 4C are schematic diagrams illustrating a gradual closing of an atraumatic forceps.
Figure 4B:
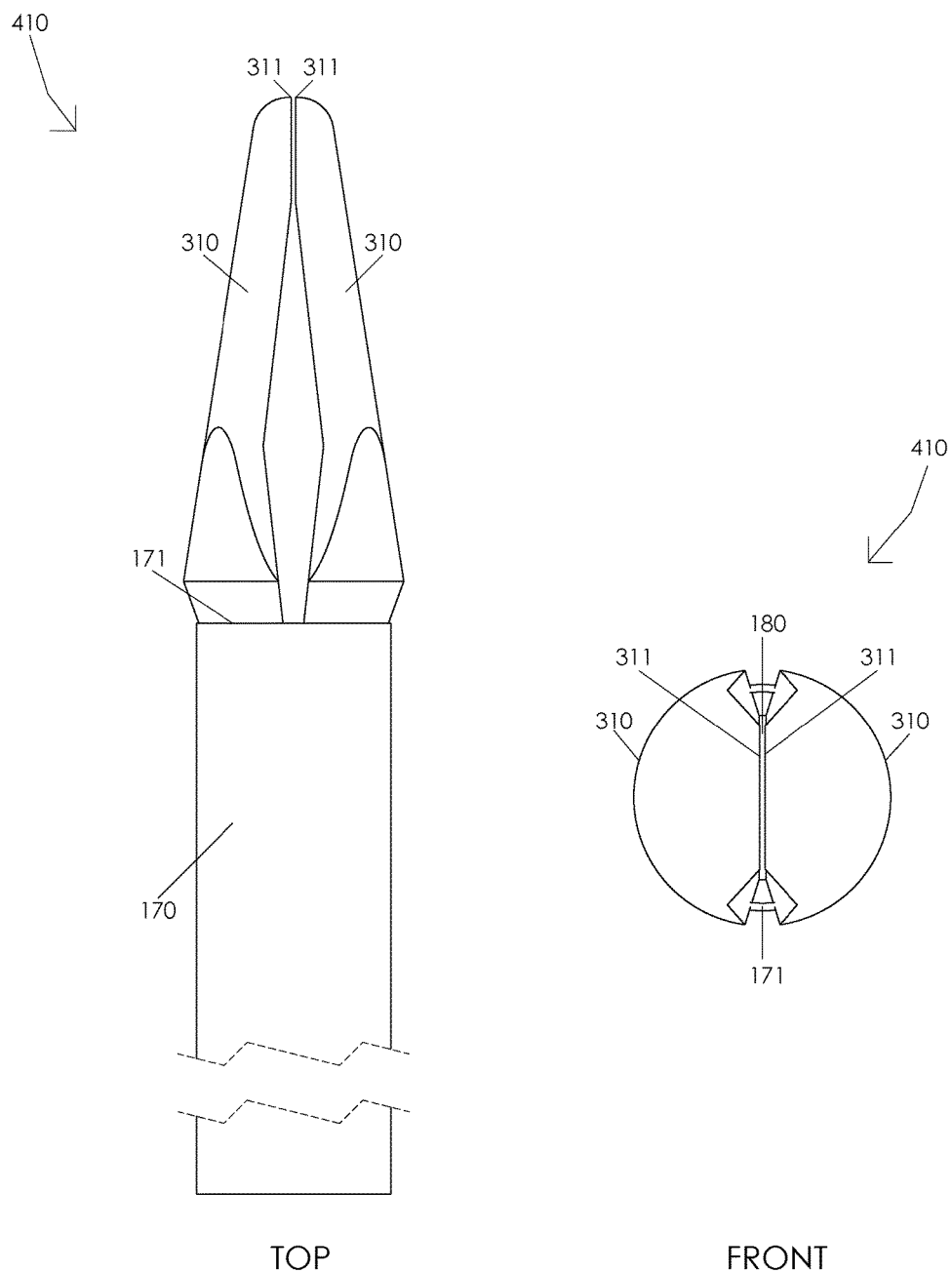
Figure 4C:
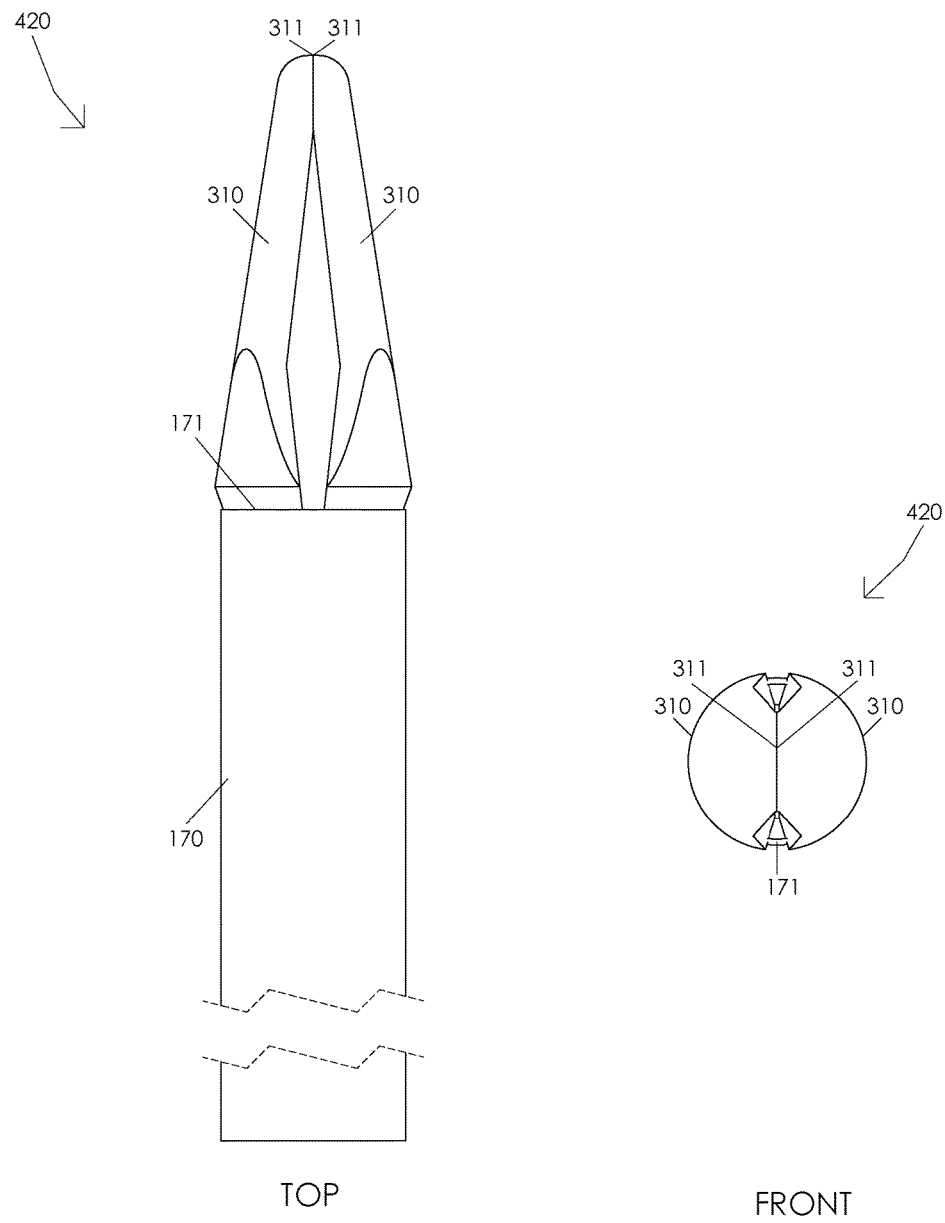

FIGS. 4A, 4B, and 4C are schematic diagrams illustrating a gradual closing of an atraumatic forceps 300. FIG. 4A illustrates a top view and a front view of an open atraumatic forceps 400. In one or more embodiments, atraumatic forceps 300 may comprise an open atraumatic forceps 400, e.g., when a first atraumatic forceps jaw distal end 311 is separated from a second atraumatic forceps jaw distal end 311 by distance 315. Illustratively, atraumatic forceps 300 may comprise an open atraumatic forceps 400, e.g., when outer hypodermic tube 170 is fully retracted relative to atraumatic forceps jaws proximal ends 312. Illustratively, atraumatic forceps 300 may comprise an open atraumatic forceps 400, e.g., when handle 110 is fully decompressed.

FIG. 4B illustrates a top view and a front view of a partially closed atraumatic forceps 410. In one or more embodiments, a compression of handle 110 may be configured to gradually close an atraumatic forceps 300, e.g., from an open atraumatic forceps 400 to a partially closed atraumatic forceps 410. Illustratively, a compression of handle 110 may be configured to extend outer hypodermic tube 170 relative to surgical blank 180, e.g., a compression of handle 110 may be configured to extend outer hypodermic tube distal end 171 over atraumatic forceps jaws proximal ends 312. In one or more embodiments, a compression of handle 110 may be configured to decrease a distance between a first atraumatic forceps jaw distal end 311 and a second atraumatic forceps jaw distal end 311, e.g., a first atraumatic forceps jaw distal end 311 and a second atraumatic forceps jaw distal end 311 may be separated by a distance less than distance 315 when atraumatic forceps 300 comprises a partially closed atraumatic forceps 410.

FIG. 4C illustrates a top view and a front view of a fully closed atraumatic forceps 420. Illustratively, a compression of handle 110 may be configured to gradually close an atraumatic forceps 300, e.g., from a partially closed atraumatic forceps 410 to a fully closed atraumatic forceps 420. In one or more embodiments, a compression of handle 110 may be configured to extend outer hypodermic tube 170 relative to surgical blank 180, e.g., a compression of handle 110 may be configured to extend outer hypodermic tube distal end 171 over atraumatic forceps jaws proximal ends 312. Illustratively, an extension of outer hypodermic tube 170 over atraumatic forceps jaws proximal ends 312 may be configured to close atraumatic forceps jaws 310 wherein atraumatic forceps jaws 310 initially contact at atraumatic forceps jaws distal ends 311. In one or more embodiments, a compression of handle 110 may be configured to gradually close atraumatic forceps jaws 310 wherein atraumatic forceps jaws 310 initially contact at atraumatic forceps jaws distal ends 311. Illustratively, after atraumatic forceps jaws distal ends 311 initially contact, a compression of handle 110 may be configured to gradually close atraumatic forceps jaws 310 wherein a contact area between atraumatic forceps jaws 310 gradually increases. In one or more embodiments, atraumatic forceps jaws 310 may be configured to close wherein an amount of a first atraumatic forceps jaw 310 in contact with a second atraumatic forceps jaw 310 increases gradually from atraumatic forceps jaws distal ends 311, e.g., atraumatic forceps jaws 310 may be configured to close wherein an amount of a first atraumatic forceps jaw 310 in contact with a second atraumatic forceps jaw 310 increases gradually towards atraumatic forceps jaws proximal ends 312. Illustratively, a compression of handle 110 may be configured to close atraumatic forceps jaws 310 starting at atraumatic forceps jaws distal ends 311 and gradually progressing towards atraumatic forceps jaws proximal ends 312. In one or more embodiments, a compression of handle 110 may be configured to close a first atraumatic forceps jaw 310 and a second atraumatic forceps jaw 310 wherein the first and second atraumatic forceps jaws 310 initially contact each other at first and second atraumatic forceps jaws distal ends 311. Illustratively, after the first and second atraumatic forceps jaws 310 initially contact at first and second atraumatic forceps jaws distal ends 311, a compression of handle 110 may be configured to cause medial portions of the first and second atraumatic forceps jaws 310 to gradually contact each other starting at medial portions of the first and second atraumatic forceps jaws 310 adjacent to first and second atraumatic forceps jaws distal ends 311.

In one or more embodiments, a surgeon may separate an internal limiting membrane from a retina by grasping the internal limiting membrane with atraumatic forceps jaws 310, e.g., without damaging the retina. Illustratively, a surgeon may manipulate handle 110 and assembled surgical instrument 200 to approach a retina with atraumatic forceps 300, e.g., when atraumatic forceps 300 comprises an open atraumatic forceps 400. For example, a surgeon may gradually move atraumatic forceps jaws distal ends 311 closer to a retina until atraumatic forceps jaws distal ends 311 contact an internal limiting membrane. In one or more embodiments, a compression of handle 110, e.g., by a surgeon, may be configured to extend outer hypodermic tube 170 over atraumatic forceps jaws proximal ends 312. Illustratively, a surgeon may grasp an internal limiting membrane with atraumatic forceps jaws distal ends 311 and no other portion of atraumatic forceps jaws 310, e.g., to minimize trauma to an underlying retinal tissue. For example, after a surgeon grasps a first portion of an internal limiting membrane with atraumatic forceps jaws distal ends 311, the surgeon may manipulate the first portion of the internal limiting membrane and compress handle 110 to grasp a second portion of the internal limiting membrane with atraumatic forceps jaws 310. Illustratively, the surgeon may grasp the second portion of the internal limiting membrane with a portion of atraumatic forceps jaws 310 located a distance from atraumatic forceps jaws distal ends 311.

Figure 5A:
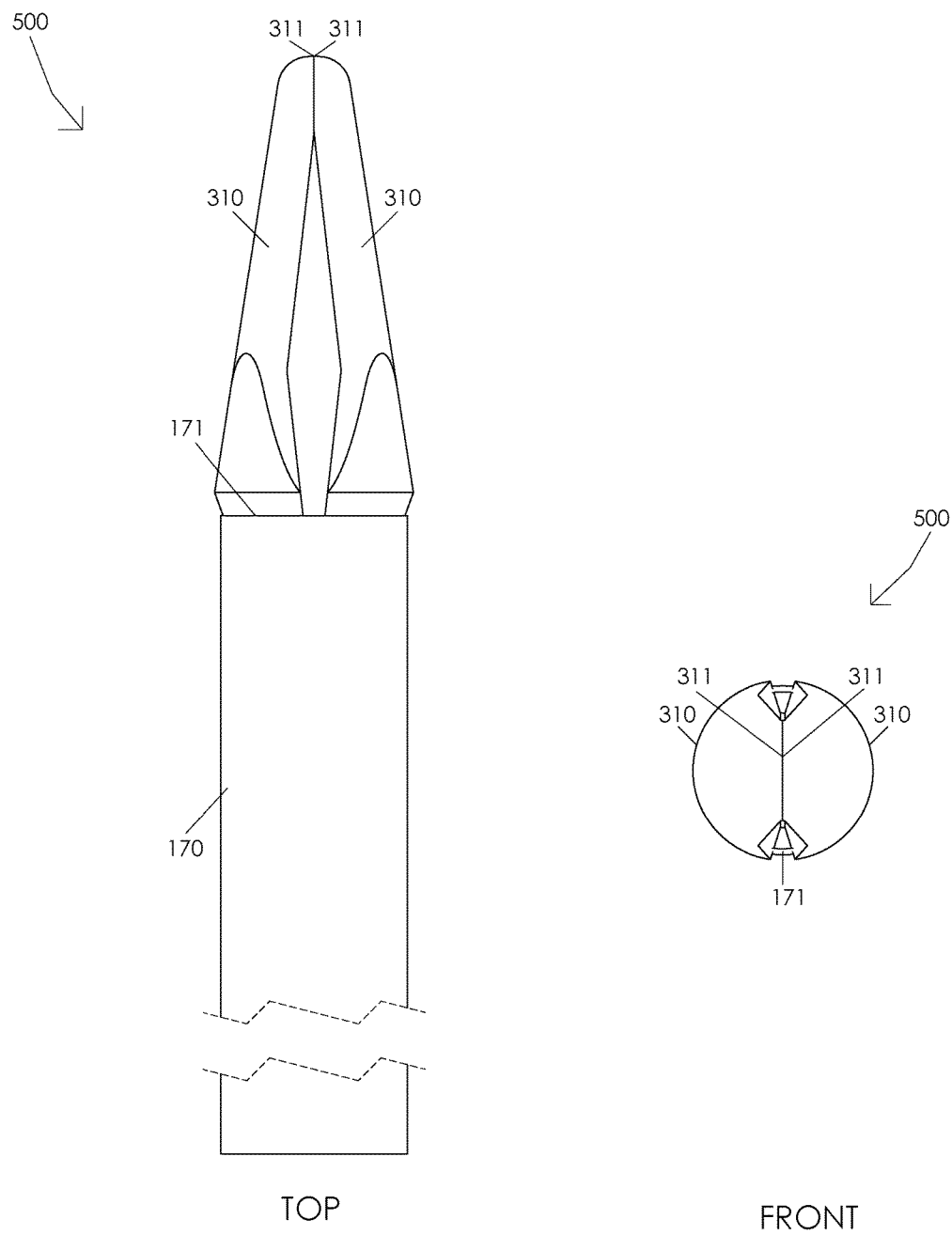
FIGS. 5A, 5B, and 5C are schematic diagrams illustrating a gradual opening of an atraumatic forceps.
Figure 5B:
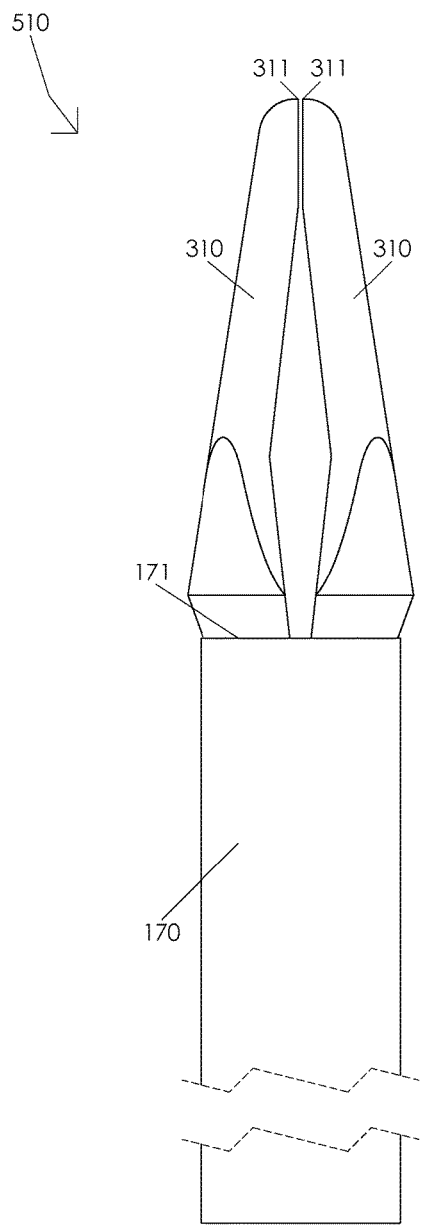
Figure 5B:
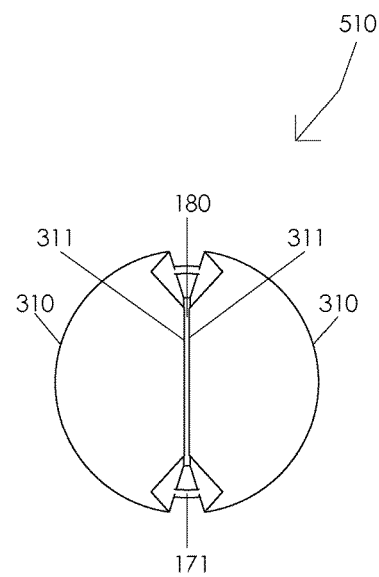
Figure 5C:
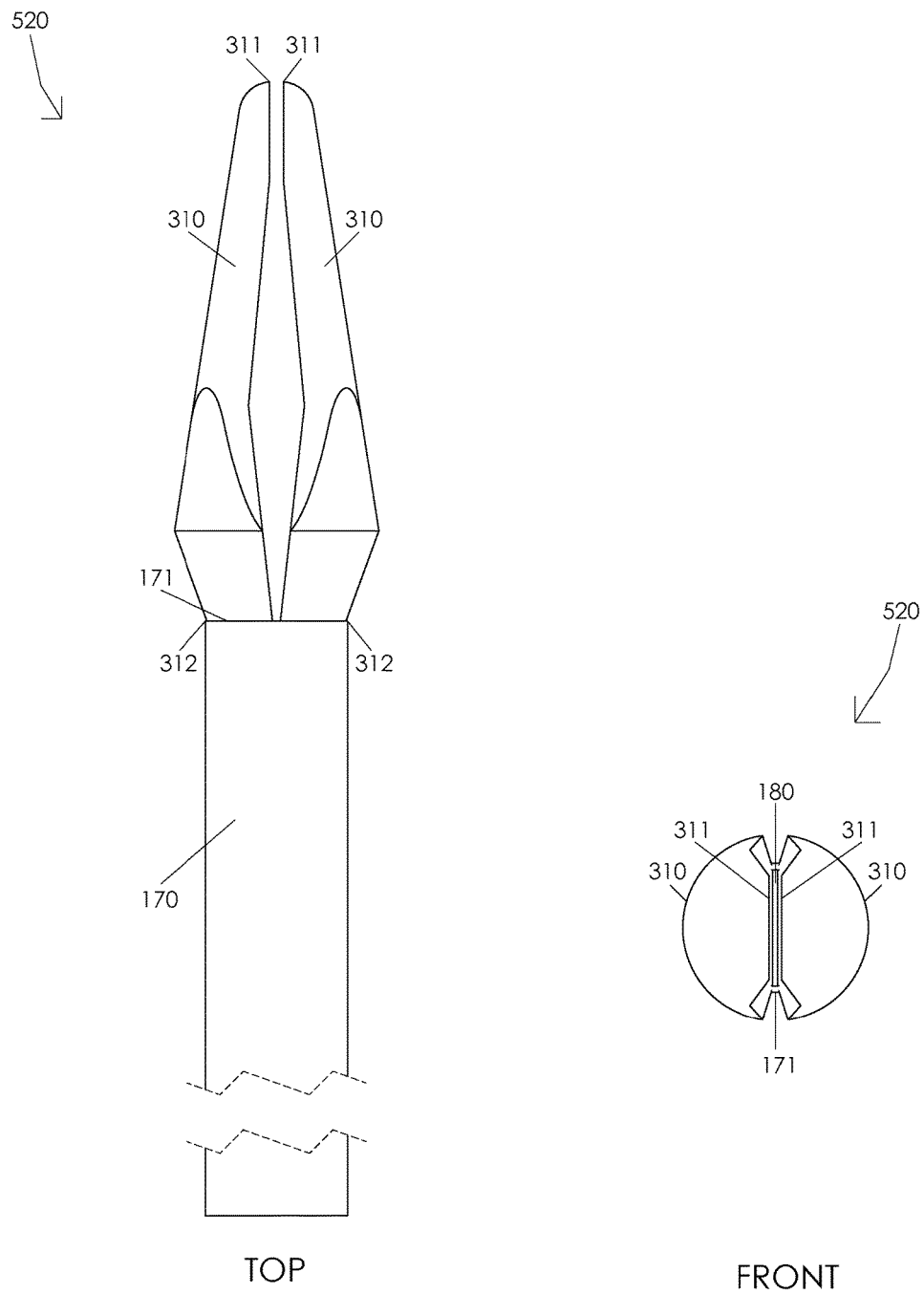

FIGS. 5A, 5B, and 5C are schematic diagrams illustrating a gradual opening of an atraumatic forceps 300. FIG. 5A illustrates a top view and a front view of a closed atraumatic forceps 500. In one or more embodiments, atraumatic forceps 300 may comprise a closed atraumatic forceps 500, e.g., when a first atraumatic forceps jaw distal end 311 is adjacent to a second atraumatic forceps jaw distal end 311. Illustratively, atraumatic forceps 300 may comprise a closed atraumatic forceps 500, e.g., when outer hypodermic tube 170 is fully extended over atraumatic forceps jaws proximal ends 312. Illustratively, atraumatic forceps 300 may comprise a closed atraumatic forceps 500, e.g., when handle 110 is fully compressed.

FIG. 5B illustrates a top view and a front view of a partially open atraumatic forceps 510. In one or more embodiments, a decompression of handle 110 may be configured to gradually open an atraumatic forceps 300, e.g., from a closed atraumatic forceps 500 to a partially open atraumatic forceps 510. Illustratively, a decompression of handle 110 may be configured to retract outer hypodermic tube 170 relative to surgical blank 180, e.g., a decompression of handle 110 may be configured to retract outer hypodermic tube distal end 171 relative to atraumatic forceps jaws proximal ends 312. In one or more embodiments, a decompression of handle 110 may be configured to gradually separate atraumatic forceps jaws 310. Illustratively, a decompression of handle 110 may be configured to gradually separate atraumatic forceps jaws 310 wherein a first atraumatic forceps jaw distal end 311 contacts a second atraumatic forceps jaw distal end 311 until all other portions of atraumatic forceps jaws 310 are separated. In one or more embodiments, a decompression of handle 110 may be configured to separate atraumatic forceps jaws 310 wherein atraumatic forceps jaws distal ends 311 are the last portions of atraumatic forceps jaws 310 to separate.

FIG. 5C illustrates a top view and a front view of a fully open atraumatic forceps 520. Illustratively, a decompression of handle 110 may be configured to gradually open an atraumatic forceps 300, e.g., from a partially open atraumatic forceps 510 to a fully open atraumatic forceps 520. In one or more embodiments, a decompression of handle 110 may be configured to retract outer hypodermic tube 170 relative to surgical blank 180, e.g., a decompression of handle 110 may be configured to retract outer hypodermic tube distal end 171 relative to atraumatic forceps jaws proximal ends 312. Illustratively, a decompression of handle 110 may be configured to gradually separate atraumatic forceps jaws 310. In one or more embodiments, a first atraumatic forceps jaw distal end 311 and a second atraumatic forceps jaw distal end 311 may be separated by distance 315, e.g., when atraumatic forceps 300 comprises a fully open atraumatic forceps 520.

Figure 6:
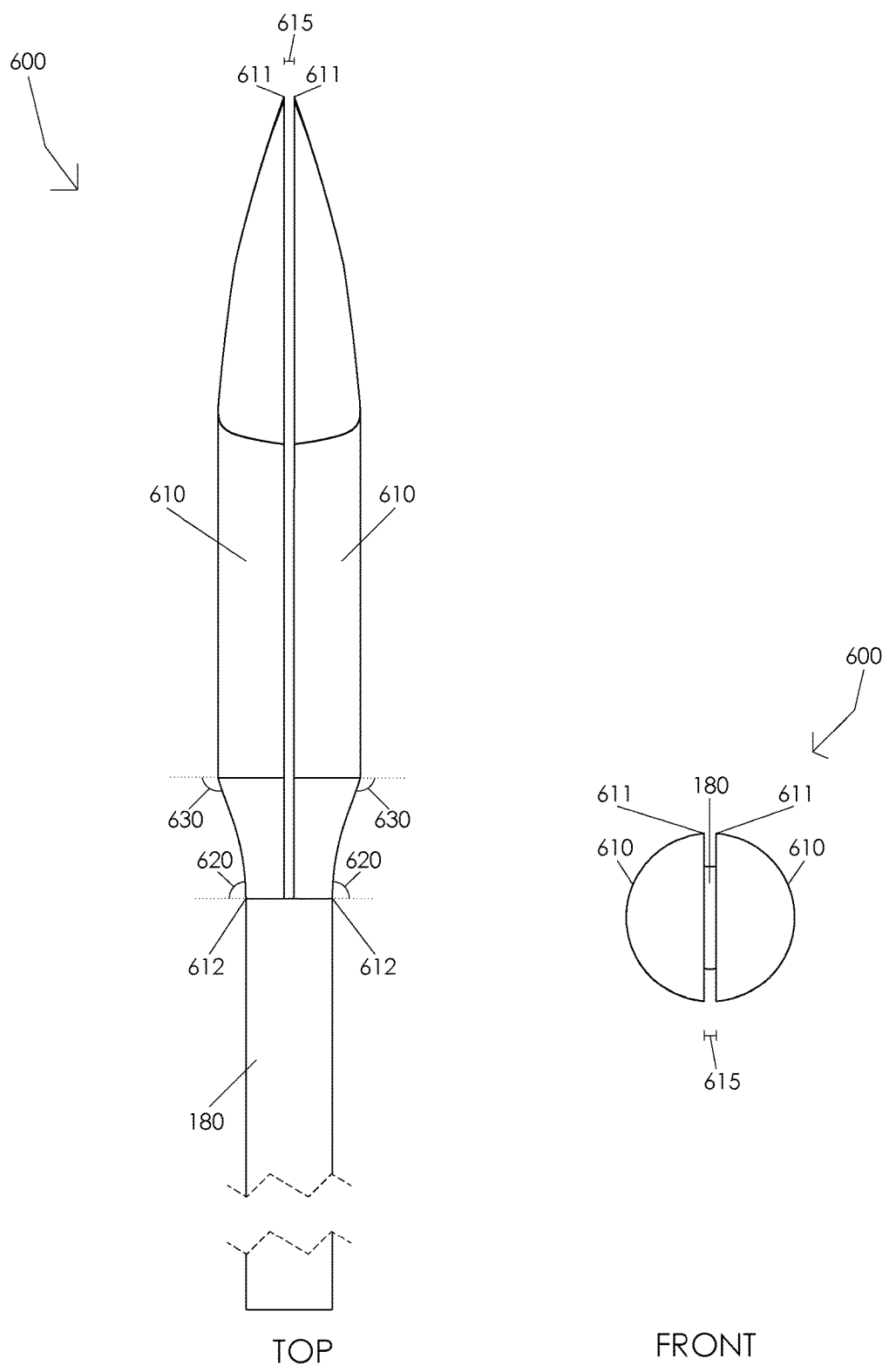
FIG. 6 is a schematic diagram illustrating an atraumatic forceps.

FIG. 6 is a schematic diagram illustrating an atraumatic forceps 600. FIG. 6 illustrates a top view and a front view of an atraumatic forceps 600. Illustratively, atraumatic forceps 600 may be manufactured with dimensions configured for performing microsurgical procedures, e.g., ophthalmic surgical procedures. In one or more embodiments, atraumatic forceps 600 may be manufactured from surgical blank 180. Illustratively, atraumatic forceps 600 may be manufactured by modifying surgical blank 180, e.g., with an electric discharge machine. In one or more embodiments, atraumatic forceps 600 may be manufactured by modifying surgical blank 180, e.g., with a laser, a file, or any suitable modification means. Illustratively, atraumatic forceps 600 may comprise a plurality of atraumatic forceps jaws 610, a fourth contour angle 620, and a fifth contour angle 630.

Illustratively, each atraumatic forceps jaw 610 of a plurality of atraumatic forceps jaws 610 may comprise an atraumatic forceps jaw distal end 611 and an atraumatic forceps jaw proximal end 612. In one or more embodiments, a first atraumatic forceps jaw distal end 611 and a second atraumatic forceps jaw distal end 611 may be separated by a distance 615. Illustratively, distance 615 may comprise a distance in a range of 0.005 to 0.08 inches, e.g., distance 615 may comprise a distance of 0.04 inches. In one or more embodiments, distance 615 may comprise a distance less than 0.005 inches or greater than 0.08 inches. Illustratively, atraumatic forceps 600 may be configured to separate a first tissue from a surface of a second tissue without damaging the second tissue. For example, atraumatic forceps 600 may be configured to separate a first tissue having a convex surface geometry from a second tissue having a convex surface geometry without damaging the second tissue. In one or more embodiments, the first tissue may comprise an internal limiting membrane and the second tissue may comprise a retina. Illustratively, distance 615 may comprise a distance in a range of 200 to 600 times an average thickness of the first tissue, e.g., distance 615 may comprise a distance 291 times the average thickness of the first tissue. In one or more embodiments, distance 615 may comprise a distance less than 200 times or greater than 600 times the average thickness of the first tissue. Illustratively, distance 615 may comprise a distance in a range of 200 to 600 times an average thickness of an internal limiting membrane, e.g., distance 615 may comprise a distance 291 times the average thickness of an internal limiting membrane. In one or more embodiments, distance 615 may comprise a distance less than 200 times or greater than 600 times the average thickness of an internal limiting membrane.

Illustratively, fourth contour angle 620 may comprise any angle less than 90 degrees, e.g., fourth contour angle 620 may comprise an angle in a range of 60 to 80 degrees. In one or more embodiments, fourth contour angle 620 may comprise an angle less than 60 degrees or greater than 80 degrees. Illustratively, fourth contour angle 620 may comprise a 76.3 degree angle. In one or more embodiments, fifth contour angle 630 may comprise any angle greater than 90 degrees, e.g., fifth contour angle 630 may comprise an angle in a range of 95 to 120 degrees. Illustratively, fifth contour angle 630 may comprise an angle less than 95 degrees or greater than 120 degrees. In one or more embodiments, fifth contour angle 630 may comprise a 103.7 degree angle.

In one or more embodiments, atraumatic forceps jaws 610 may be configured to close at atraumatic forceps jaws distal ends 611 as outer hypodermic tube 170 is gradually actuated over atraumatic forceps jaws proximal ends 612. Illustratively, an extension of outer hypodermic tube 170 relative to surgical blank 180 may be configured to decrease a distance 615 between a first atraumatic forceps jaw distal end 611 and a second atraumatic forceps jaw distal end 611. In one or more embodiments, an extension of outer hypodermic tube 170 over a first atraumatic forceps jaw proximal end 612 and a second atraumatic forceps jaw proximal end 612 may be configured to cause the first atraumatic forceps jaw distal end 611 and the second atraumatic forceps jaw distal end 611 to contact before any other portion of the first atraumatic forceps jaw 610 contacts any other portion of the second atraumatic forceps jaw 610.

Figure 7A:
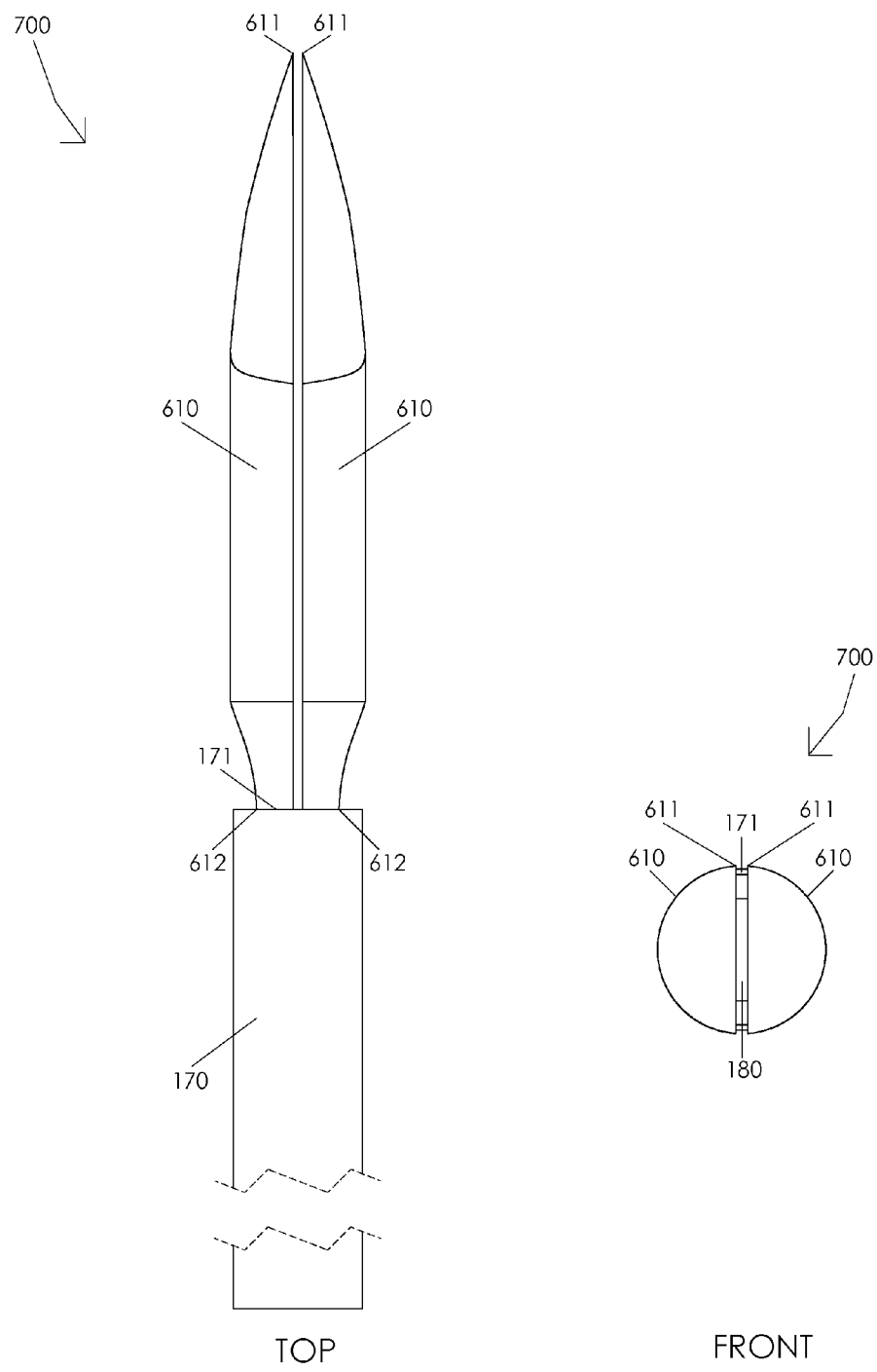
FIGS. 7A, 7B, and 7C are schematic diagrams illustrating a gradual closing of an atraumatic forceps.
Figure 7B:
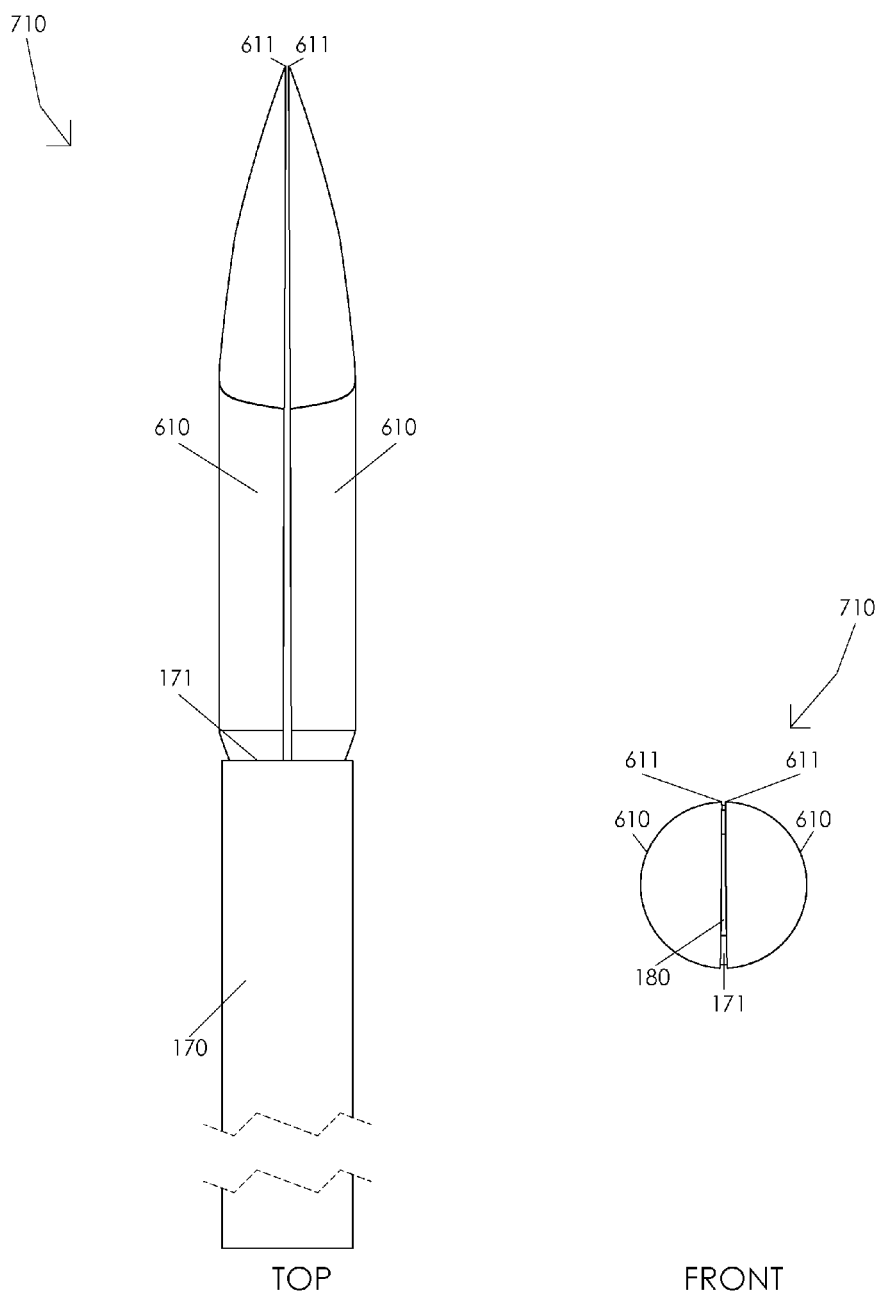
Figure 7C:
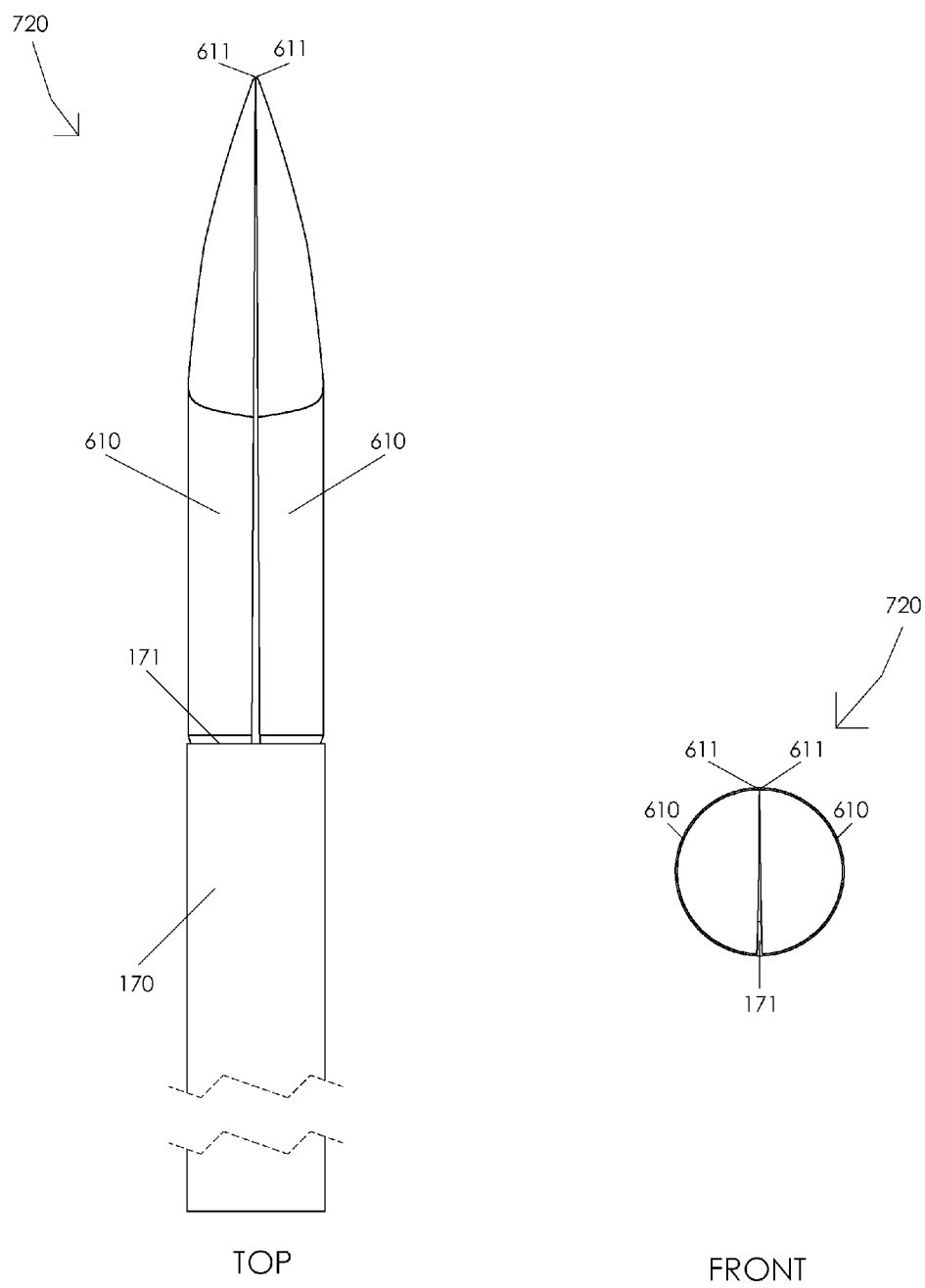

FIGS. 7A, 7B, and 7C are schematic diagrams illustrating a gradual closing of an atraumatic forceps 600. FIG. 7A illustrates a top view and a front view of an open atraumatic forceps 700. In one or more embodiments, atraumatic forceps 600 may comprise an open atraumatic forceps 700, e.g., when a first atraumatic forceps jaw distal end 611 is separated from a second atraumatic forceps jaw distal end 611 by distance 615. Illustratively, atraumatic forceps 600 may comprise an open atraumatic forceps 700, e.g., when outer hypodermic tube 170 is fully retracted relative to atraumatic forceps jaws proximal ends 612. Illustratively, atraumatic forceps 600 may comprise an open atraumatic forceps 700, e.g., when handle 110 is fully decompressed.

FIG. 7B illustrates a top view and a front view of a partially closed atraumatic forceps 710. In one or more embodiments, a compression of handle 110 may be configured to gradually close an atraumatic forceps 600, e.g., from an open atraumatic forceps 700 to a partially closed atraumatic forceps 710. Illustratively, a compression of handle 110 may be configured to extend outer hypodermic tube 170 relative to surgical blank 180, e.g., a compression of handle 110 may be configured to extend outer hypodermic tube distal end 171 over atraumatic forceps jaws proximal ends 612. In one or more embodiments, a compression of handle 110 may be configured to decrease a distance between a first atraumatic forceps jaw distal end 611 and a second atraumatic forceps jaw distal end 611, e.g., a first atraumatic forceps jaw distal end 611 and a second atraumatic forceps jaw distal end 611 may be separated by a distance less than distance 615 when atraumatic forceps 600 comprises a partially closed atraumatic forceps 710.

FIG. 7C illustrates a top view and a front view of a fully closed atraumatic forceps 720. Illustratively, a compression of handle 110 may be configured to gradually close an atraumatic forceps 600, e.g., from a partially closed atraumatic forceps 710 to a fully closed atraumatic forceps 720. In one or more embodiments, a compression of handle 110 may be configured to extend outer hypodermic tube 170 relative to surgical blank 180, e.g., a compression of handle 110 may be configured to extend outer hypodermic tube distal end 171 over atraumatic forceps jaws proximal ends 612. Illustratively, an extension of outer hypodermic tube 170 over atraumatic forceps jaws proximal ends 612 may be configured to close atraumatic forceps jaws 610 wherein atraumatic forceps jaws 610 initially contact at atraumatic forceps jaws distal ends 611. In one or more embodiments, a compression of handle 110 may be configured to gradually close atraumatic forceps jaws 610 wherein atraumatic forceps jaws 610 initially contact at atraumatic forceps jaws distal ends 611. Illustratively, after atraumatic forceps jaws distal ends 611 initially contact, a compression of handle 110 may be configured to gradually close atraumatic forceps jaws 610 wherein a contact area between atraumatic forceps jaws 610 gradually increases. In one or more embodiments, atraumatic forceps jaws 610 may be configured to close wherein an amount of a first atraumatic forceps jaw 610 in contact with a second atraumatic forceps jaw 610 increases gradually from atraumatic forceps jaws distal ends 611, e.g., atraumatic forceps jaws 610 may be configured to close wherein an amount of a first atraumatic forceps jaw 610 in contact with a second atraumatic forceps jaw 610 increases gradually towards atraumatic forceps jaws proximal ends 612. Illustratively, a compression of handle 110 may be configured to close atraumatic forceps jaws 610 starting at atraumatic forceps jaws distal ends 611 and gradually progressing towards atraumatic forceps jaws proximal ends 612. In one or more embodiments, a compression of handle 110 may be configured to close a first atraumatic forceps jaw 610 and a second atraumatic forceps jaw 610 wherein the first and second atraumatic forceps jaws 610 initially contact each other at first and second atraumatic forceps jaws distal ends 611. Illustratively, after the first and second atraumatic forceps jaws 610 initially contact at first and second atraumatic forceps jaws distal ends 611, a compression of handle 110 may be configured to cause medial portions of the first and second atraumatic forceps jaws 610 to gradually contact each other starting at medial portions of the first and second atraumatic forceps jaws 610 adjacent to first and second atraumatic forceps jaws distal ends 611.

In one or more embodiments, a surgeon may separate an internal limiting membrane from a retina by grasping the internal limiting membrane with atraumatic forceps jaws 610, e.g., without damaging the retina. Illustratively, a surgeon may manipulate handle 110 and assembled surgical instrument 200 to approach a retina with atraumatic forceps 600, e.g., when atraumatic forceps 600 comprises an open atraumatic forceps 700. For example, a surgeon may gradually move atraumatic forceps jaws distal ends 611 closer to a retina until atraumatic forceps jaws distal ends 611 contact an internal limiting membrane. In one or more embodiments, a compression of handle 110, e.g., by a surgeon, may be configured to extend outer hypodermic tube 170 over atraumatic forceps jaws proximal ends 612. Illustratively, a surgeon may grasp an internal limiting membrane with atraumatic forceps jaws distal ends 611 and no other portion of atraumatic forceps jaws 610, e.g., to minimize trauma to an underlying retinal tissue. For example, after a surgeon grasps a first portion of an internal limiting membrane with atraumatic forceps jaws distal ends 611, the surgeon may manipulate the first portion of the internal limiting membrane and compress handle 110 to grasp a second portion of the internal limiting membrane with atraumatic forceps jaws 610. Illustratively, the surgeon may grasp the second portion of the internal limiting membrane with a portion of atraumatic forceps jaws 610 located a distance from atraumatic forceps jaws distal ends 611.

Figure 8A:
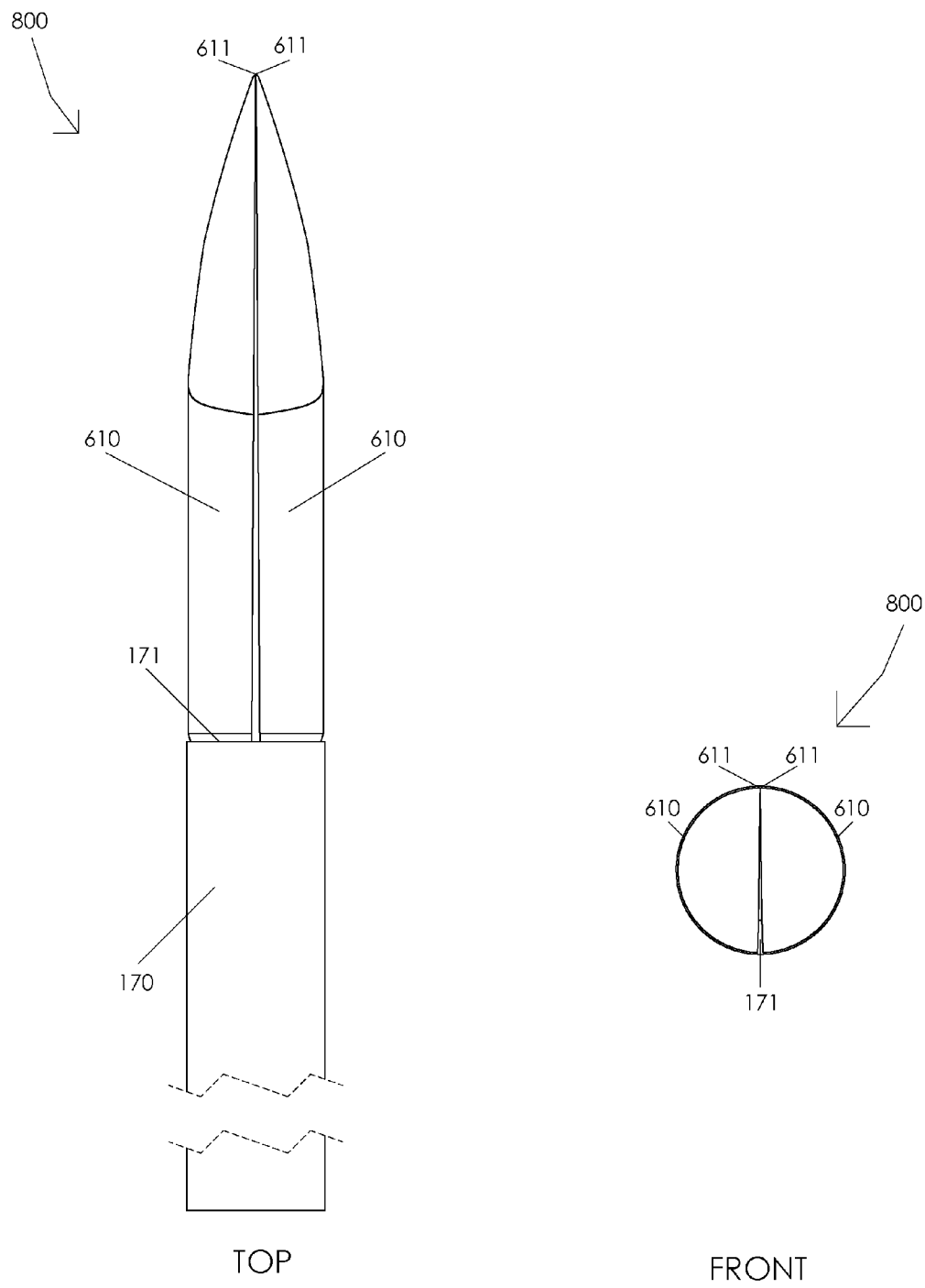
FIGS. 8A, 8B, and 8C are schematic diagrams illustrating a gradual opening of an atraumatic forceps.
Figure 8B:
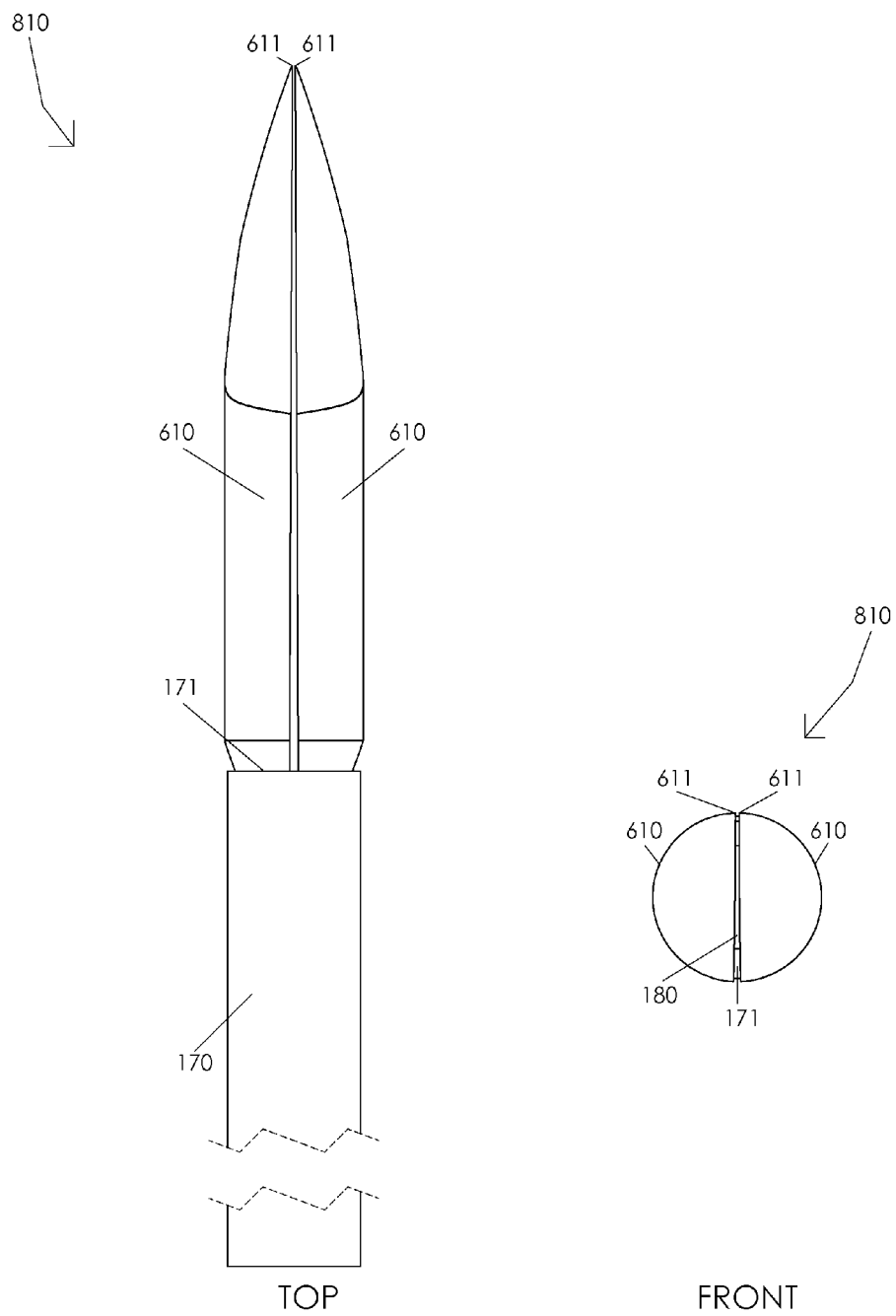
Figure 8C:
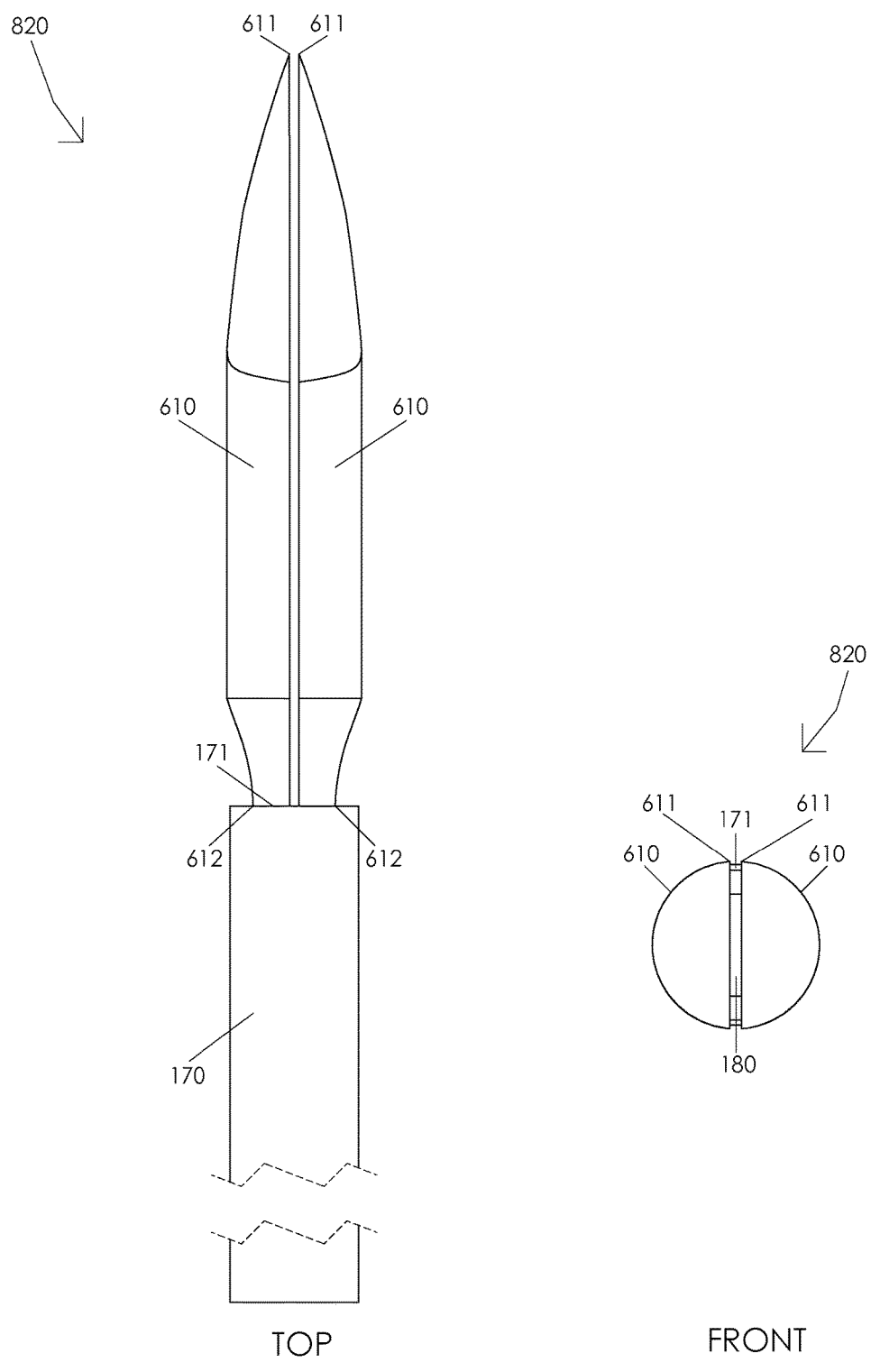

FIGS. 8A, 8B, and 8C are schematic diagrams illustrating a gradual opening of an atraumatic forceps 600. FIG. 8A illustrates a top view and a front view of a closed atraumatic forceps 800. In one or more embodiments, atraumatic forceps 600 may comprise a closed atraumatic forceps 800, e.g., when a first atraumatic forceps jaw distal end 611 is adjacent to a second atraumatic forceps jaw distal end 611. Illustratively, atraumatic forceps 600 may comprise a closed atraumatic forceps 800, e.g., when outer hypodermic tube 170 is fully extended over atraumatic forceps jaws proximal ends 612. Illustratively, atraumatic forceps 600 may comprise a closed atraumatic forceps 800, e.g., when handle 110 is fully compressed.

FIG. 8B illustrates a top view and a front view of a partially open atraumatic forceps 810. In one or more embodiments, a decompression of handle 110 may be configured to gradually open an atraumatic forceps 600, e.g., from a closed atraumatic forceps 800 to a partially open atraumatic forceps 810. Illustratively, a decompression of handle 110 may be configured to retract outer hypodermic tube 170 relative to surgical blank 180, e.g., a decompression of handle 110 may be configured to retract outer hypodermic tube distal end 171 relative to atraumatic forceps jaws proximal ends 612. In one or more embodiments, a decompression of handle 110 may be configured to gradually separate atraumatic forceps jaws 610. Illustratively, a decompression of handle 110 may be configured to gradually separate atraumatic forceps jaws 610 wherein a first atraumatic forceps jaw distal end 611 contacts a second atraumatic forceps jaw distal end 611 until all other portions of atraumatic forceps jaws 610 are separated. In one or more embodiments, a decompression of handle 110 may be configured to separate atraumatic forceps jaws 610 wherein atraumatic forceps jaws distal ends 611 are the last portions of atraumatic forceps jaws 610 to separate.

FIG. 8C illustrates a top view and a front view of a fully open atraumatic forceps 820. Illustratively, a decompression of handle 110 may be configured to gradually open an atraumatic forceps 600, e.g., from a partially open atraumatic forceps 810 to a fully open atraumatic forceps 820. In one or more embodiments, a decompression of handle 110 may be configured to retract outer hypodermic tube 170 relative to surgical blank 180, e.g., a decompression of handle 110 may be configured to retract outer hypodermic tube distal end 171 relative to atraumatic forceps jaws proximal ends 612. Illustratively, a decompression of handle 110 may be configured to gradually separate atraumatic forceps jaws 610. In one or more embodiments, a first atraumatic forceps jaw distal end 611 and a second atraumatic forceps jaw distal end 611 may be separated by distance 615, e.g., when atraumatic forceps 600 comprises a fully open atraumatic forceps 820.

Figure 9:
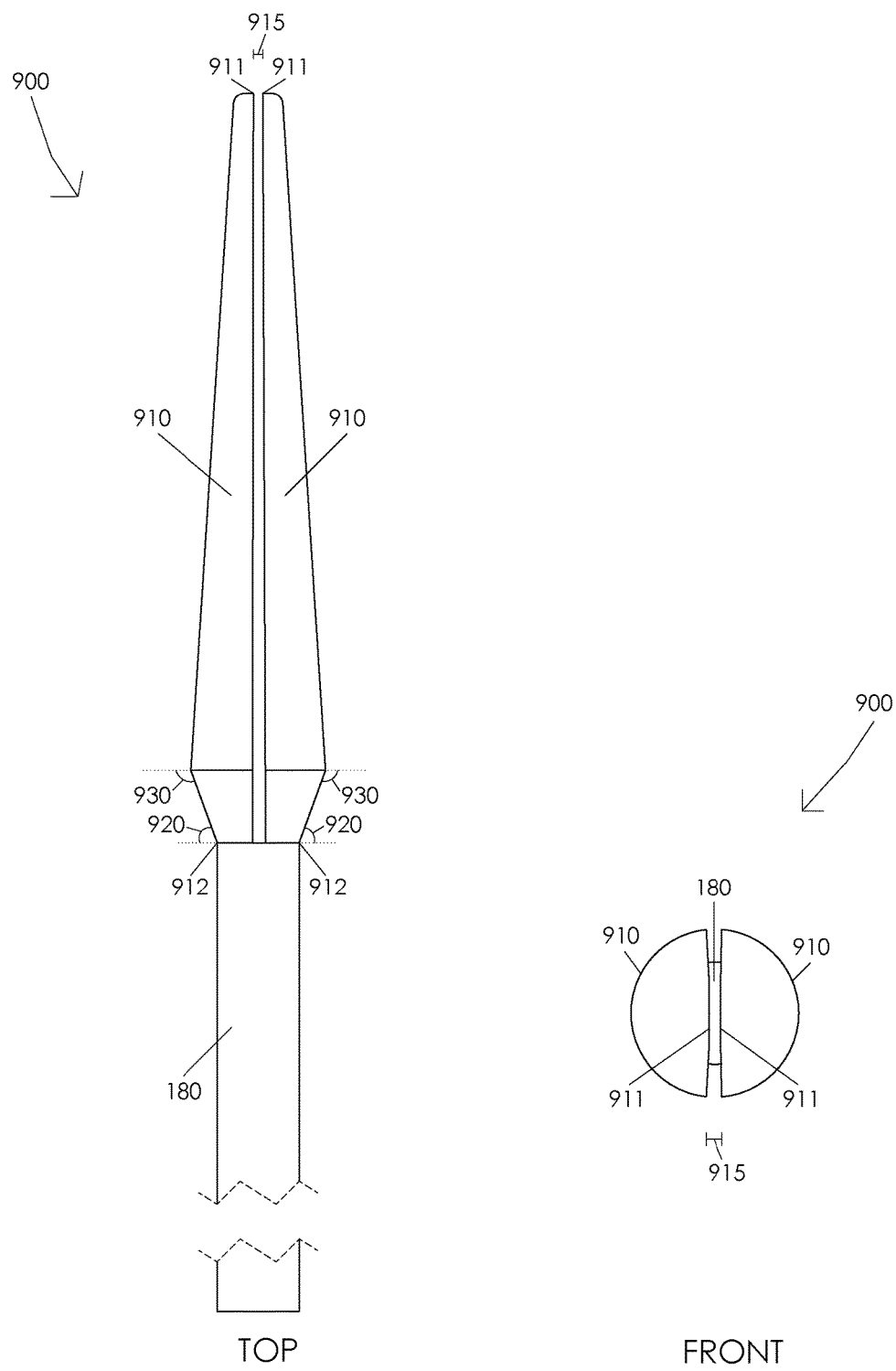
FIG. 9 is a schematic diagram illustrating an atraumatic forceps.

FIG. 9 is a schematic diagram illustrating an atraumatic forceps 900. FIG. 9 illustrates a top view and a front view of an atraumatic forceps 900. Illustratively, atraumatic forceps 900 may be manufactured with dimensions configured for performing microsurgical procedures, e.g., ophthalmic surgical procedures. In one or more embodiments, atraumatic forceps 900 may be manufactured from surgical blank 180. Illustratively, atraumatic forceps 900 may be manufactured by modifying surgical blank 180, e.g., with an electric discharge machine. In one or more embodiments, atraumatic forceps 900 may be manufactured by modifying surgical blank 180, e.g., with a laser, a file, or any suitable modification means. Illustratively, atraumatic forceps 900 may comprise a plurality of atraumatic forceps jaws 910, a sixth contour angle 920, and a seventh contour angle 930.

Illustratively, each atraumatic forceps jaw 910 of a plurality of atraumatic forceps jaws 910 may comprise an atraumatic forceps jaw distal end 911 and an atraumatic forceps jaw proximal end 912. In one or more embodiments, a first atraumatic forceps jaw distal end 911 and a second atraumatic forceps jaw distal end 911 may be separated by a distance 915. Illustratively, distance 915 may comprise a distance in a range of 0.005 to 0.08 inches, e.g., distance 915 may comprise a distance of 0.04 inches. In one or more embodiments, distance 915 may comprise a distance less than 0.005 inches or greater than 0.08 inches. Illustratively, atraumatic forceps 900 may be configured to separate a first tissue from a surface of a second tissue without damaging the second tissue. For example, atraumatic forceps 900 may be configured to separate a first tissue having a convex surface geometry from a second tissue having a convex surface geometry without damaging the second tissue. In one or more embodiments, the first tissue may comprise an internal limiting membrane and the second tissue may comprise a retina. Illustratively, distance 915 may comprise a distance in a range of 200 to 600 times an average thickness of the first tissue, e.g., distance 915 may comprise a distance 291 times the average thickness of the first tissue. In one or more embodiments, distance 915 may comprise a distance less than 200 times or greater than 600 times the average thickness of the first tissue. Illustratively, distance 915 may comprise a distance in a range of 200 to 600 times an average thickness of an internal limiting membrane, e.g., distance 915 may comprise a distance 291 times the average thickness of an internal limiting membrane. In one or more embodiments, distance 915 may comprise a distance less than 200 times or greater than 600 times the average thickness of an internal limiting membrane.

Illustratively, sixth contour angle 920 may comprise any angle less than 90 degrees, e.g., sixth contour angle 920 may comprise an angle in a range of 60 to 80 degrees. In one or more embodiments, sixth contour angle 920 may comprise an angle less than 60 degrees or greater than 80 degrees. Illustratively, sixth contour angle 920 may comprise a 70 degree angle. In one or more embodiments, seventh contour angle 930 may comprise any angle greater than 90 degrees, e.g., seventh contour angle 930 may comprise an angle in a range of 95 to 120 degrees. Illustratively, seventh contour angle 930 may comprise an angle less than 95 degrees or greater than 120 degrees. In one or more embodiments, seventh contour angle 930 may comprise a 110 degree angle.

In one or more embodiments, atraumatic forceps jaws 910 may be configured to close at atraumatic forceps jaws distal ends 911 as outer hypodermic tube 170 is gradually actuated over atraumatic forceps jaws proximal ends 912. Illustratively, an extension of outer hypodermic tube 170 relative to surgical blank 180 may be configured to decrease a distance 915 between a first atraumatic forceps jaw distal end 911 and a second atraumatic forceps jaw distal end 911. In one or more embodiments, an extension of outer hypodermic tube 170 over a first atraumatic forceps jaw proximal end 912 and a second atraumatic forceps jaw proximal end 912 may be configured to cause the first atraumatic forceps jaw distal end 911 and the second atraumatic forceps jaw distal end 911 to contact before any other portion of the first atraumatic forceps jaw 910 contacts any other portion of the second atraumatic forceps jaw 910.

Figure 10A:
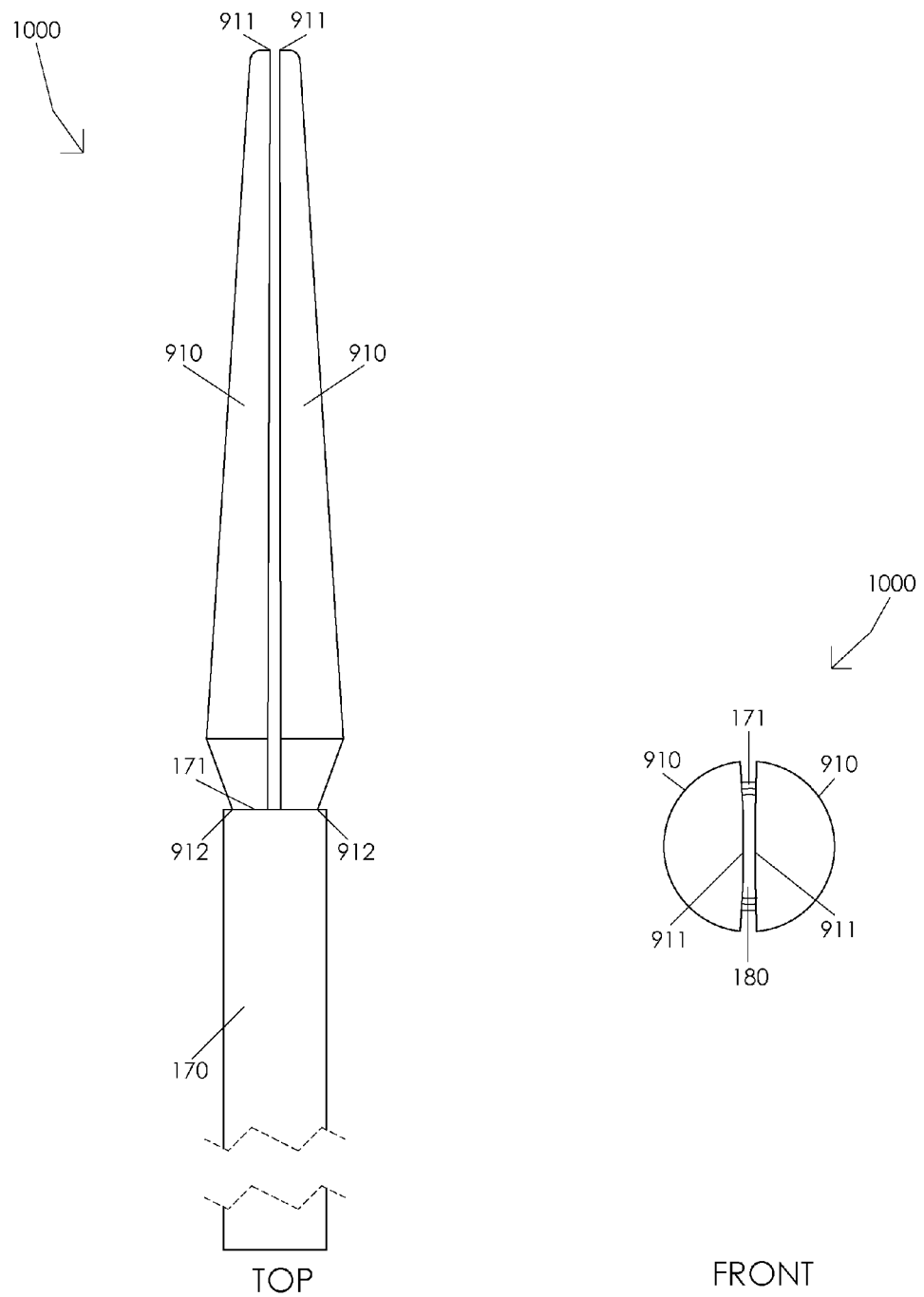
FIGS. 10A, 10B, and 10C are schematic diagrams illustrating a gradual closing of an atraumatic forceps.
Figure 10B:
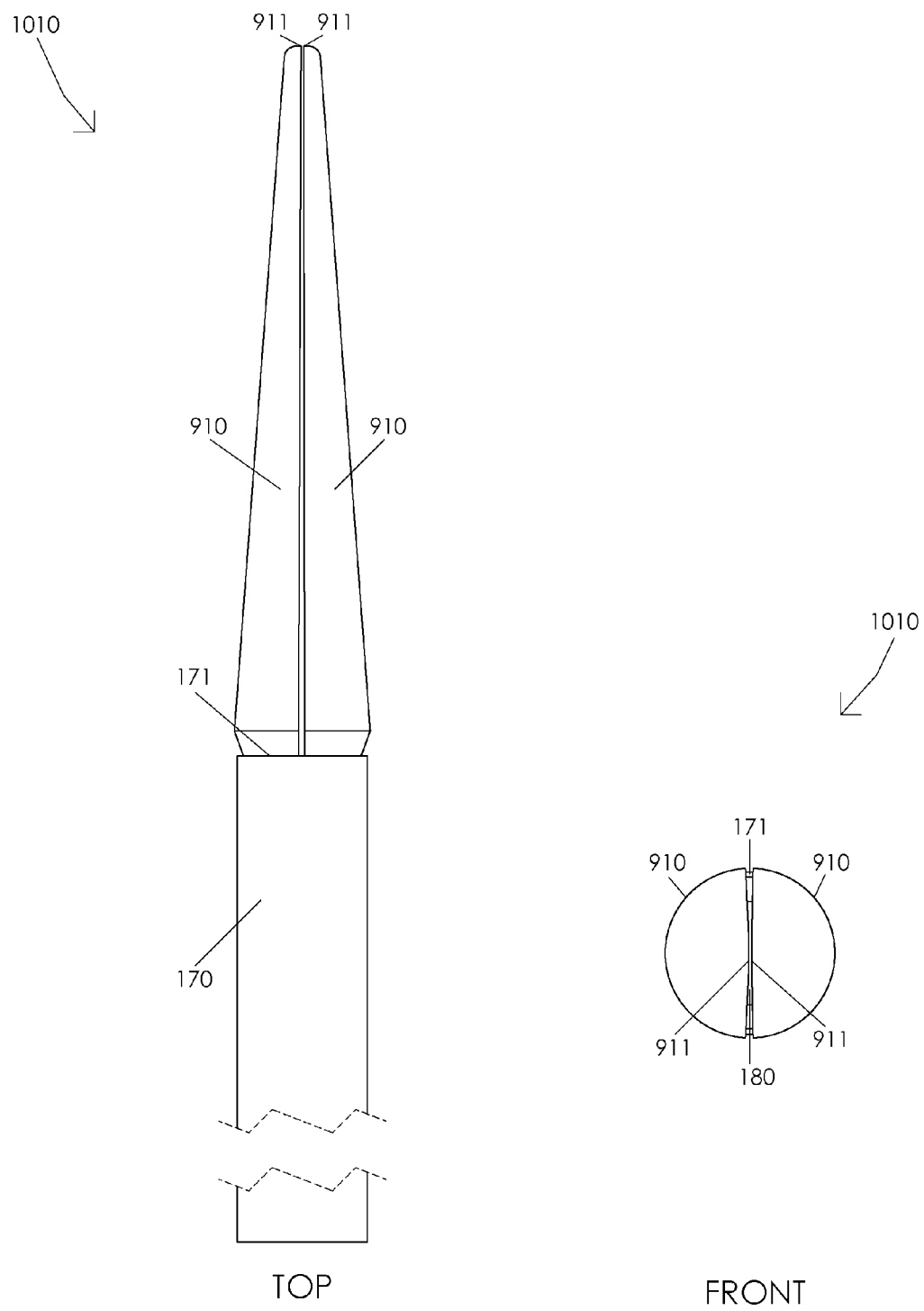
Figure 10C:
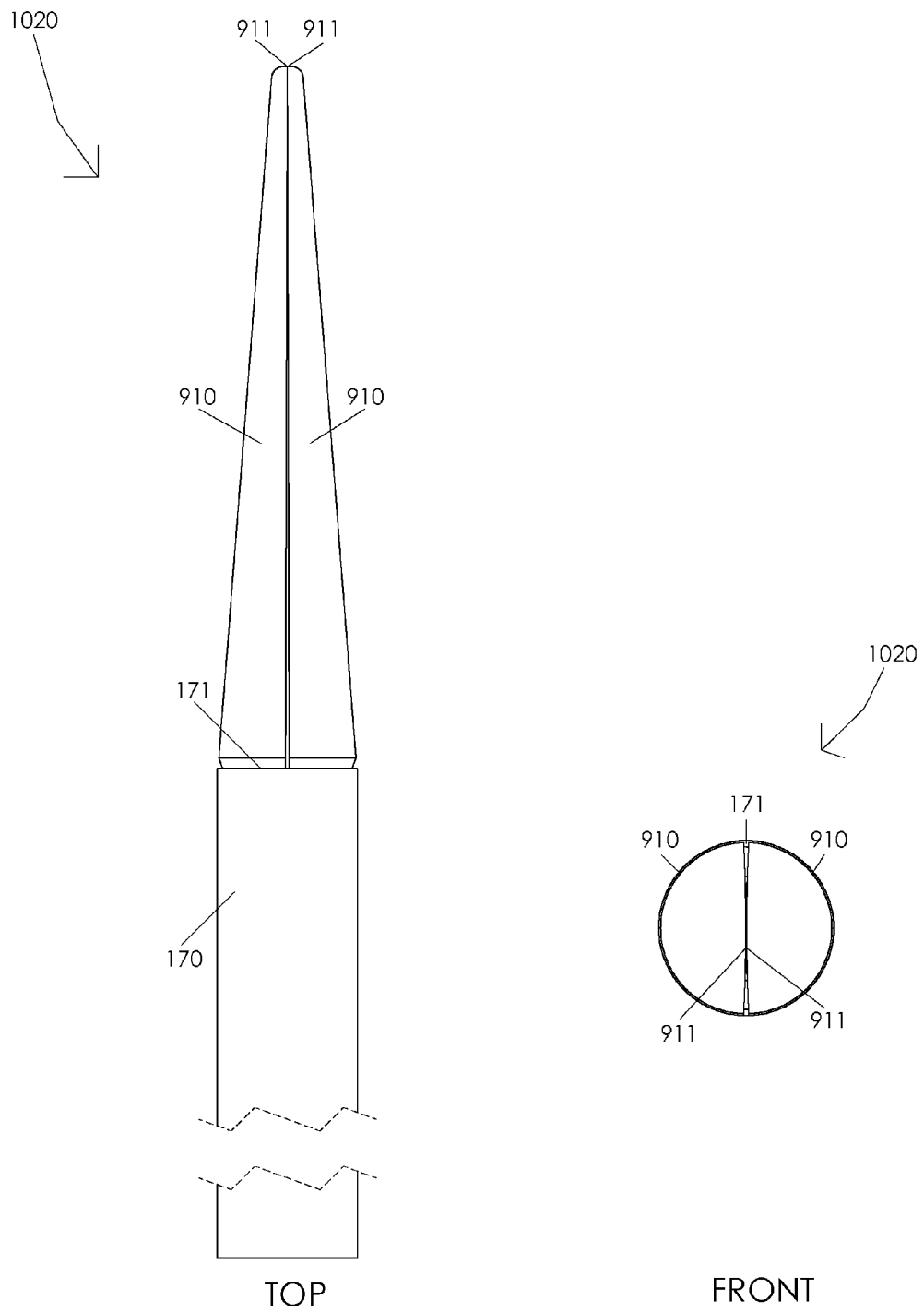

FIGS. 10A, 10B, and 10C are schematic diagrams illustrating a gradual closing of an atraumatic forceps 900. FIG. 10A illustrates a top view and a front view of an open atraumatic forceps 1000. In one or more embodiments, atraumatic forceps 900 may comprise an open atraumatic forceps 1000, e.g., when a first atraumatic forceps jaw distal end 911 is separated from a second atraumatic forceps jaw distal end 911 by distance 915. Illustratively, atraumatic forceps 900 may comprise an open atraumatic forceps 1000, e.g., when outer hypodermic tube 170 is fully retracted relative to atraumatic forceps jaws proximal ends 912. Illustratively, atraumatic forceps 900 may comprise an open atraumatic forceps 1000, e.g., when handle 110 is fully decompressed.

FIG. 10B illustrates a top view and a front view of a partially closed atraumatic forceps 1010. In one or more embodiments, a compression of handle 110 may be configured to gradually close an atraumatic forceps 900, e.g., from an open atraumatic forceps 1000 to a partially closed atraumatic forceps 1010. Illustratively, a compression of handle 110 may be configured to extend outer hypodermic tube 170 relative to surgical blank 180, e.g., a compression of handle 110 may be configured to extend outer hypodermic tube distal end 171 over atraumatic forceps jaws proximal ends 912. In one or more embodiments, a compression of handle 110 may be configured to decrease a distance between a first atraumatic forceps jaw distal end 911 and a second atraumatic forceps jaw distal end 911, e.g., a first atraumatic forceps jaw distal end 911 and a second atraumatic forceps jaw distal end 911 may be separated by a distance less than distance 915 when atraumatic forceps 900 comprises a partially closed atraumatic forceps 1010.

FIG. 10C illustrates a top view and a front view of a fully closed atraumatic forceps 1020. Illustratively, a compression of handle 110 may be configured to gradually close an atraumatic forceps 900, e.g., from a partially closed atraumatic forceps 1010 to a fully closed atraumatic forceps 1020. In one or more embodiments, a compression of handle 110 may be configured to extend outer hypodermic tube 170 relative to surgical blank 180, e.g., a compression of handle 110 may be configured to extend outer hypodermic tube distal end 171 over atraumatic forceps jaws proximal ends 912. Illustratively, an extension of outer hypodermic tube 170 over atraumatic forceps jaws proximal ends 912 may be configured to close atraumatic forceps jaws 910 wherein atraumatic forceps jaws 910 initially contact at atraumatic forceps jaws distal ends 911. In one or more embodiments, a compression of handle 110 may be configured to gradually close atraumatic forceps jaws 910 wherein atraumatic forceps jaws 910 initially contact at atraumatic forceps jaws distal ends 911. Illustratively, after atraumatic forceps jaws distal ends 911 initially contact, a compression of handle 110 may be configured to gradually close atraumatic forceps jaws 910 wherein a contact area between atraumatic forceps jaws 910 gradually increases. In one or more embodiments, atraumatic forceps jaws 910 may be configured to close wherein an amount of a first atraumatic forceps jaw 910 in contact with a second atraumatic forceps jaw 910 increases gradually from atraumatic forceps jaws distal ends 911, e.g., atraumatic forceps jaws 910 may be configured to close wherein an amount of a first atraumatic forceps jaw 910 in contact with a second atraumatic forceps jaw 910 increases gradually towards atraumatic forceps jaws proximal ends 912. Illustratively, a compression of handle 110 may be configured to close atraumatic forceps jaws 910 starting at atraumatic forceps jaws distal ends 911 and gradually progressing towards atraumatic forceps jaws proximal ends 912. In one or more embodiments, a compression of handle 110 may be configured to close a first atraumatic forceps jaw 910 and a second atraumatic forceps jaw 910 wherein the first and second atraumatic forceps jaws 910 initially contact each other at first and second atraumatic forceps jaws distal ends 911. Illustratively, after the first and second atraumatic forceps jaws 910 initially contact at first and second atraumatic forceps jaws distal ends 911, a compression of handle 110 may be configured to cause medial portions of the first and second atraumatic forceps jaws 910 to gradually contact each other starting at medial portions of the first and second atraumatic forceps jaws 910 adjacent to first and second atraumatic forceps jaws distal ends 911.

In one or more embodiments, a surgeon may separate an internal limiting membrane from a retina by grasping the internal limiting membrane with atraumatic forceps jaws 910, e.g., without damaging the retina. Illustratively, a surgeon may manipulate handle 110 and assembled surgical instrument 200 to approach a retina with atraumatic forceps 900, e.g., when atraumatic forceps 900 comprises an open atraumatic forceps 1000. For example, a surgeon may gradually move atraumatic forceps jaws distal ends 911 closer to a retina until atraumatic forceps jaws distal ends 911 contact an internal limiting membrane. In one or more embodiments, a compression of handle 110, e.g., by a surgeon, may be configured to extend outer hypodermic tube 170 over atraumatic forceps jaws proximal ends 912. Illustratively, a surgeon may grasp an internal limiting membrane with atraumatic forceps jaws distal ends 911 and no other portion of atraumatic forceps jaws 910, e.g., to minimize trauma to an underlying retinal tissue. For example, after a surgeon grasps a first portion of an internal limiting membrane with atraumatic forceps jaws distal ends 911, the surgeon may manipulate the first portion of the internal limiting membrane and compress handle 110 to grasp a second portion of the internal limiting membrane with atraumatic forceps jaws 910. Illustratively, the surgeon may grasp the second portion of the internal limiting membrane with a portion of atraumatic forceps jaws 910 located a distance from atraumatic forceps jaws distal ends 911.

Figure 11A:
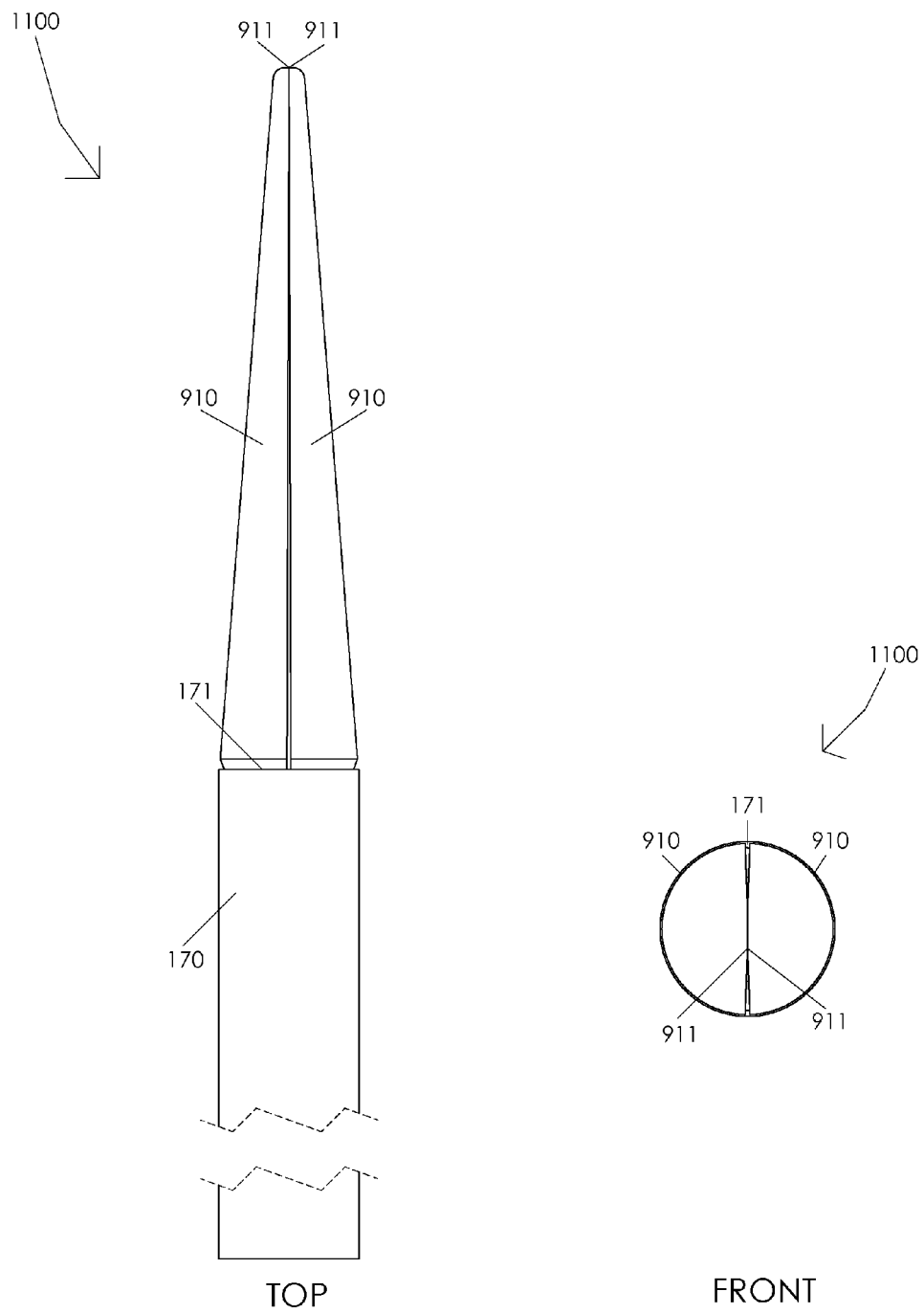
FIGS. 11A, 11B, and 11C are schematic diagrams illustrating a gradual opening of an atraumatic forceps.
Figure 11B:
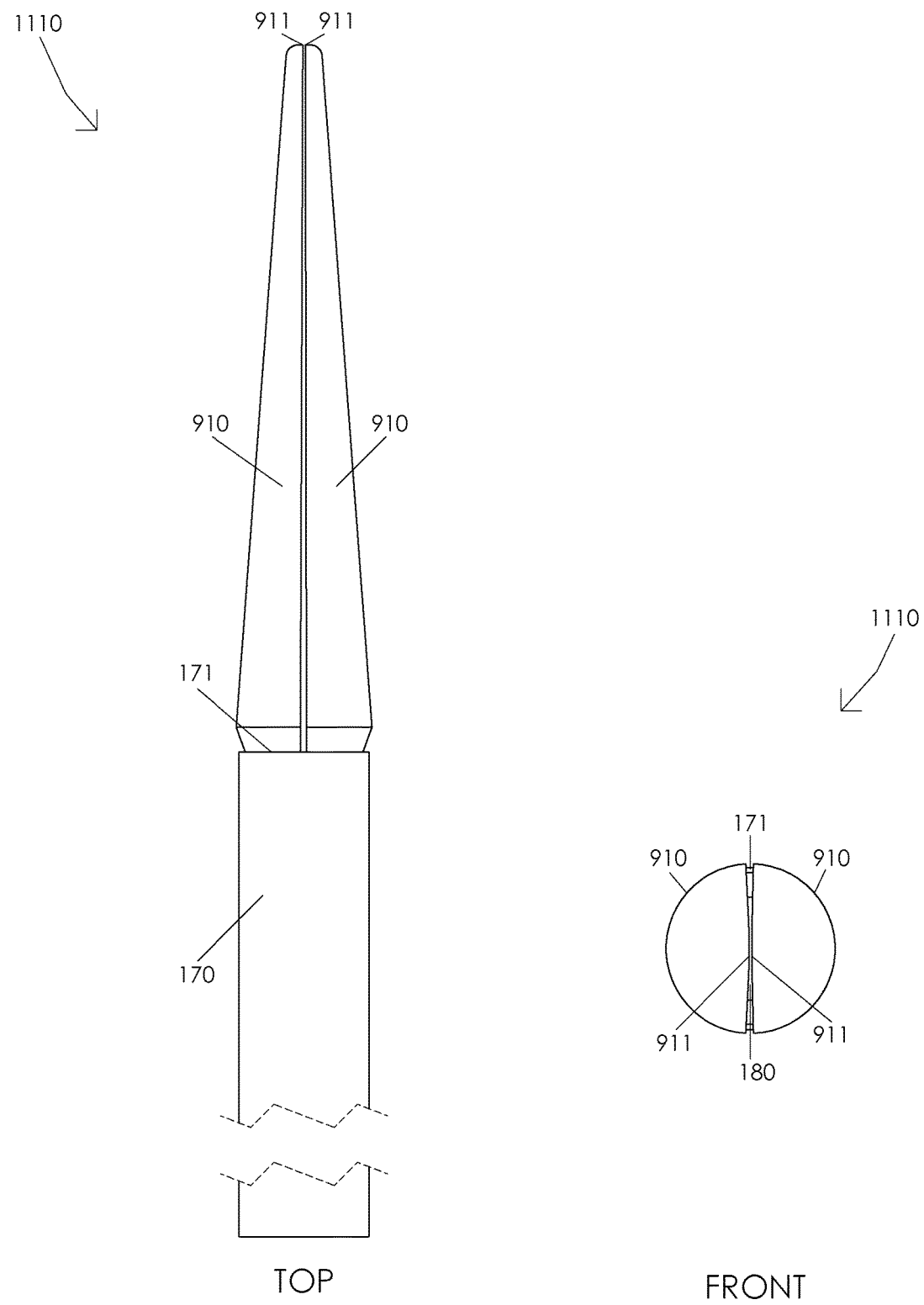
Figure 11C:
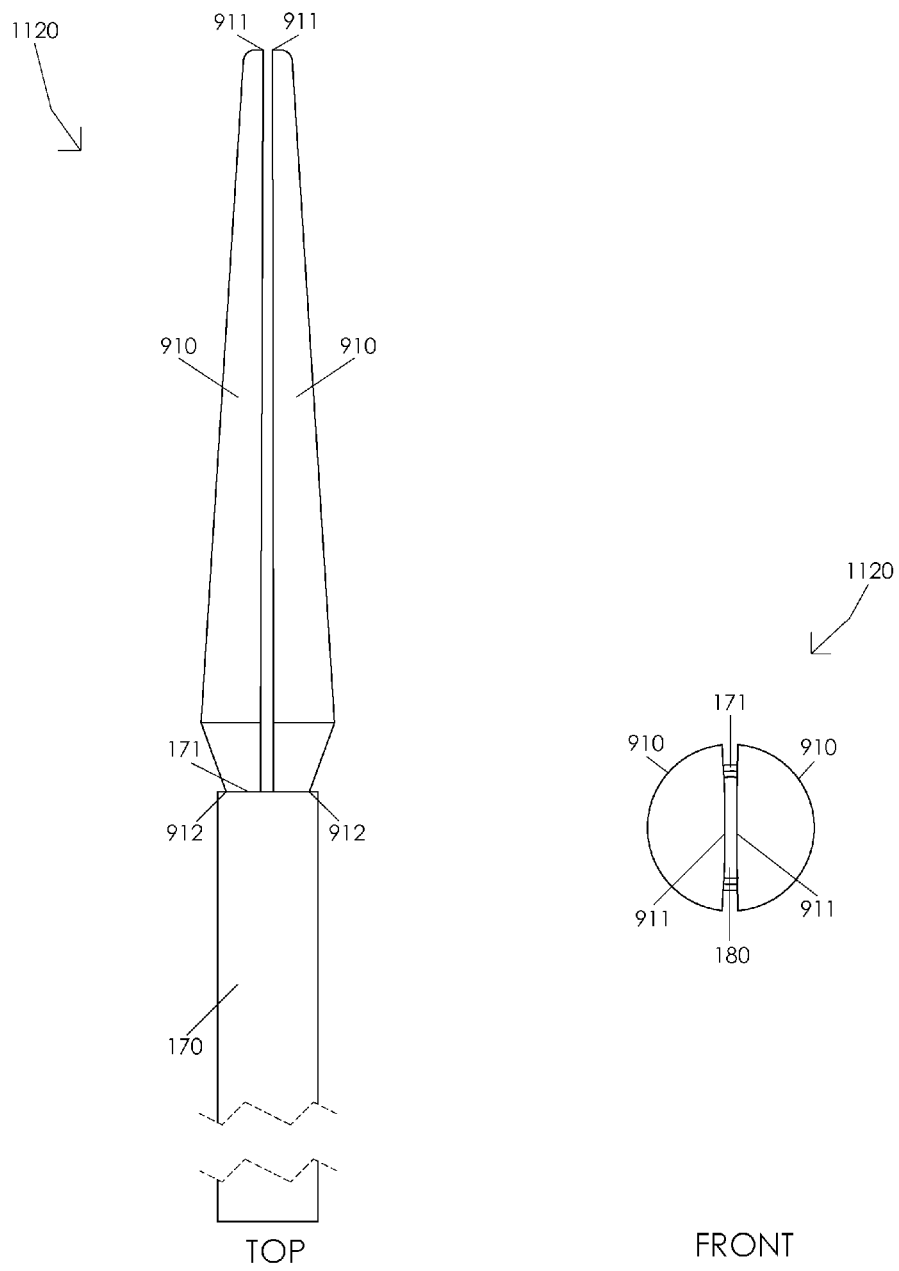

FIGS. 11A, 11B, and 11C are schematic diagrams illustrating a gradual opening of an atraumatic forceps 900. FIG. 11A illustrates a top view and a front view of a closed atraumatic forceps 1100. In one or more embodiments, atraumatic forceps 900 may comprise a closed atraumatic forceps 1100, e.g., when a first atraumatic forceps jaw distal end 911 is adjacent to a second atraumatic forceps jaw distal end 911. Illustratively, atraumatic forceps 900 may comprise a closed atraumatic forceps 1100, e.g., when outer hypodermic tube 170 is fully extended over atraumatic forceps jaws proximal ends 912. Illustratively, atraumatic forceps 900 may comprise a closed atraumatic forceps 1100, e.g., when handle 110 is fully compressed.

FIG. 11B illustrates a top view and a front view of a partially open atraumatic forceps 1110. In one or more embodiments, a decompression of handle 110 may be configured to gradually open an atraumatic forceps 900, e.g., from a closed atraumatic forceps 1100 to a partially open atraumatic forceps 1110. Illustratively, a decompression of handle 110 may be configured to retract outer hypodermic tube 170 relative to surgical blank 180, e.g., a decompression of handle 110 may be configured to retract outer hypodermic tube distal end 171 relative to atraumatic forceps jaws proximal ends 912. In one or more embodiments, a decompression of handle 110 may be configured to gradually separate atraumatic forceps jaws 910. Illustratively, a decompression of handle 110 may be configured to gradually separate atraumatic forceps jaws 910 wherein a first atraumatic forceps jaw distal end 911 contacts a second atraumatic forceps jaw distal end 911 until all other portions of atraumatic forceps jaws 910 are separated. In one or more embodiments, a decompression of handle 110 may be configured to separate atraumatic forceps jaws 910 wherein atraumatic forceps jaws distal ends 911 are the last portions of atraumatic forceps jaws 910 to separate.

FIG. 11C illustrates a top view and a front view of a fully open atraumatic forceps 1120. Illustratively, a decompression of handle 110 may be configured to gradually open an atraumatic forceps 900, e.g., from a partially open atraumatic forceps 1110 to a fully open atraumatic forceps 1120. In one or more embodiments, a decompression of handle 110 may be configured to retract outer hypodermic tube 170 relative to surgical blank 180, e.g., a decompression of handle 110 may be configured to retract outer hypodermic tube distal end 171 relative to atraumatic forceps jaws proximal ends 912. Illustratively, a decompression of handle 110 may be configured to gradually separate atraumatic forceps jaws 910. In one or more embodiments, a first atraumatic forceps jaw distal end 911 and a second atraumatic forceps jaw distal end 911 may be separated by distance 915, e.g., when atraumatic forceps 900 comprises a fully open atraumatic forceps 1120.

Figure 12:
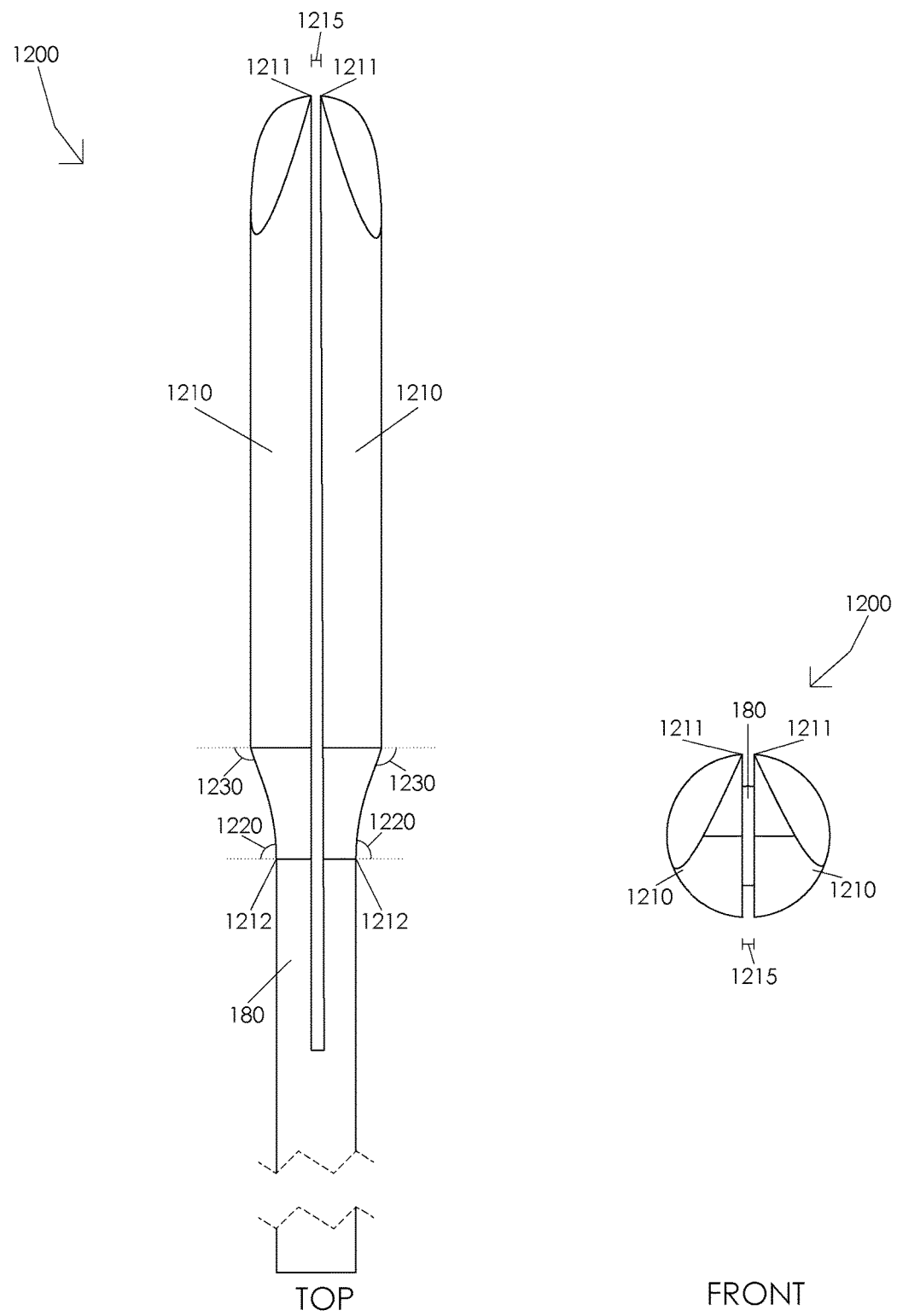
FIG. 12 is a schematic diagram illustrating an atraumatic forceps.

FIG. 12 is a schematic diagram illustrating an atraumatic forceps 1200. FIG. 12 illustrates a top view and a front view of an atraumatic forceps 1200. Illustratively, atraumatic forceps 1200 may be manufactured with dimensions configured for performing microsurgical procedures, e.g., ophthalmic surgical procedures. In one or more embodiments, atraumatic forceps 1200 may be manufactured from surgical blank 180. Illustratively, atraumatic forceps 1200 may be manufactured by modifying surgical blank 180, e.g., with an electric discharge machine. In one or more embodiments, atraumatic forceps 1200 may be manufactured by modifying surgical blank 180, e.g., with a laser, a file, or any suitable modification means. Illustratively, atraumatic forceps 1200 may comprise a plurality of atraumatic forceps jaws 1210, an eighth contour angle 1220, and a ninth contour angle 1230.

Illustratively, each atraumatic forceps jaw 1210 of a plurality of atraumatic forceps jaws 1210 may comprise an atraumatic forceps jaw distal end 1211 and an atraumatic forceps jaw proximal end 1212. In one or more embodiments, a first atraumatic forceps jaw distal end 1211 and a second atraumatic forceps jaw distal end 1211 may be separated by a distance 1215. Illustratively, distance 1215 may comprise a distance in a range of 0.005 to 0.08 inches, e.g., distance 1215 may comprise a distance of 0.04 inches. In one or more embodiments, distance 1215 may comprise a distance less than 0.005 inches or greater than 0.08 inches. Illustratively, atraumatic forceps 1200 may be configured to separate a first tissue from a surface of a second tissue without damaging the second tissue. For example, atraumatic forceps 1200 may be configured to separate a first tissue having a convex surface geometry from a second tissue having a convex surface geometry without damaging the second tissue. In one or more embodiments, the first tissue may comprise an internal limiting membrane and the second tissue may comprise a retina. Illustratively, distance 1215 may comprise a distance in a range of 200 to 600 times an average thickness of the first tissue, e.g., distance 1215 may comprise a distance 291 times the average thickness of the first tissue. In one or more embodiments, distance 1215 may comprise a distance less than 200 times or greater than 600 times the average thickness of the first tissue. Illustratively, distance 1215 may comprise a distance in a range of 200 to 600 times an average thickness of an internal limiting membrane, e.g., distance 1215 may comprise a distance 291 times the average thickness of an internal limiting membrane. In one or more embodiments, distance 1215 may comprise a distance less than 200 times or greater than 600 times the average thickness of an internal limiting membrane.

Illustratively, eighth contour angle 1220 may comprise any angle less than 90 degrees, e.g., eighth contour angle 1220 may comprise an angle in a range of 60 to 80 degrees. In one or more embodiments, eighth contour angle 1220 may comprise an angle less than 60 degrees or greater than 80 degrees. Illustratively, eighth contour angle 1220 may comprise a 72.3 degree angle. In one or more embodiments, ninth contour angle 1230 may comprise any angle greater than 90 degrees, e.g., ninth contour angle 1230 may comprise an angle in a range of 95 to 120 degrees. Illustratively, ninth contour angle 1230 may comprise an angle less than 95 degrees or greater than 120 degrees. In one or more embodiments, ninth contour angle 1230 may comprise a 107 degree angle.

In one or more embodiments, atraumatic forceps jaws 1210 may be configured to close at atraumatic forceps jaws distal ends 1211 as outer hypodermic tube 170 is gradually actuated over atraumatic forceps jaws proximal ends 1212. Illustratively, an extension of outer hypodermic tube 170 relative to surgical blank 180 may be configured to decrease a distance 1215 between a first atraumatic forceps jaw distal end 1211 and a second atraumatic forceps jaw distal end 1211. In one or more embodiments, an extension of outer hypodermic tube 170 over a first atraumatic forceps jaw proximal end 1212 and a second atraumatic forceps jaw proximal end 1212 may be configured to cause the first atraumatic forceps jaw distal end 1211 and the second atraumatic forceps jaw distal end 1211 to contact before any other portion of the first atraumatic forceps jaw 1210 contacts any other portion of the second atraumatic forceps jaw 1210.

Figure 13A:
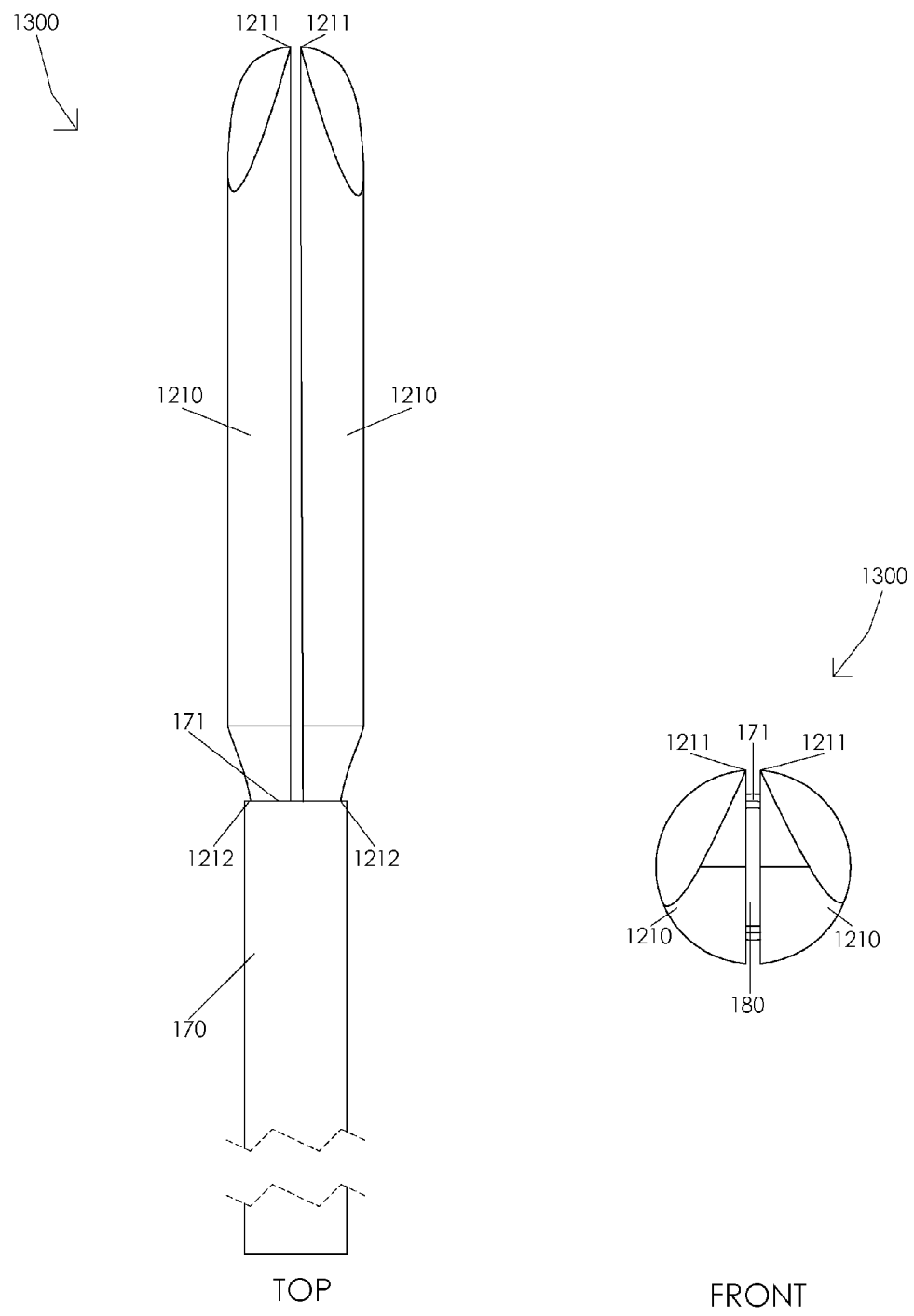
FIGS. 13A, 13B, and 13C are schematic diagrams illustrating a gradual closing of an atraumatic forceps.
Figure 13B:
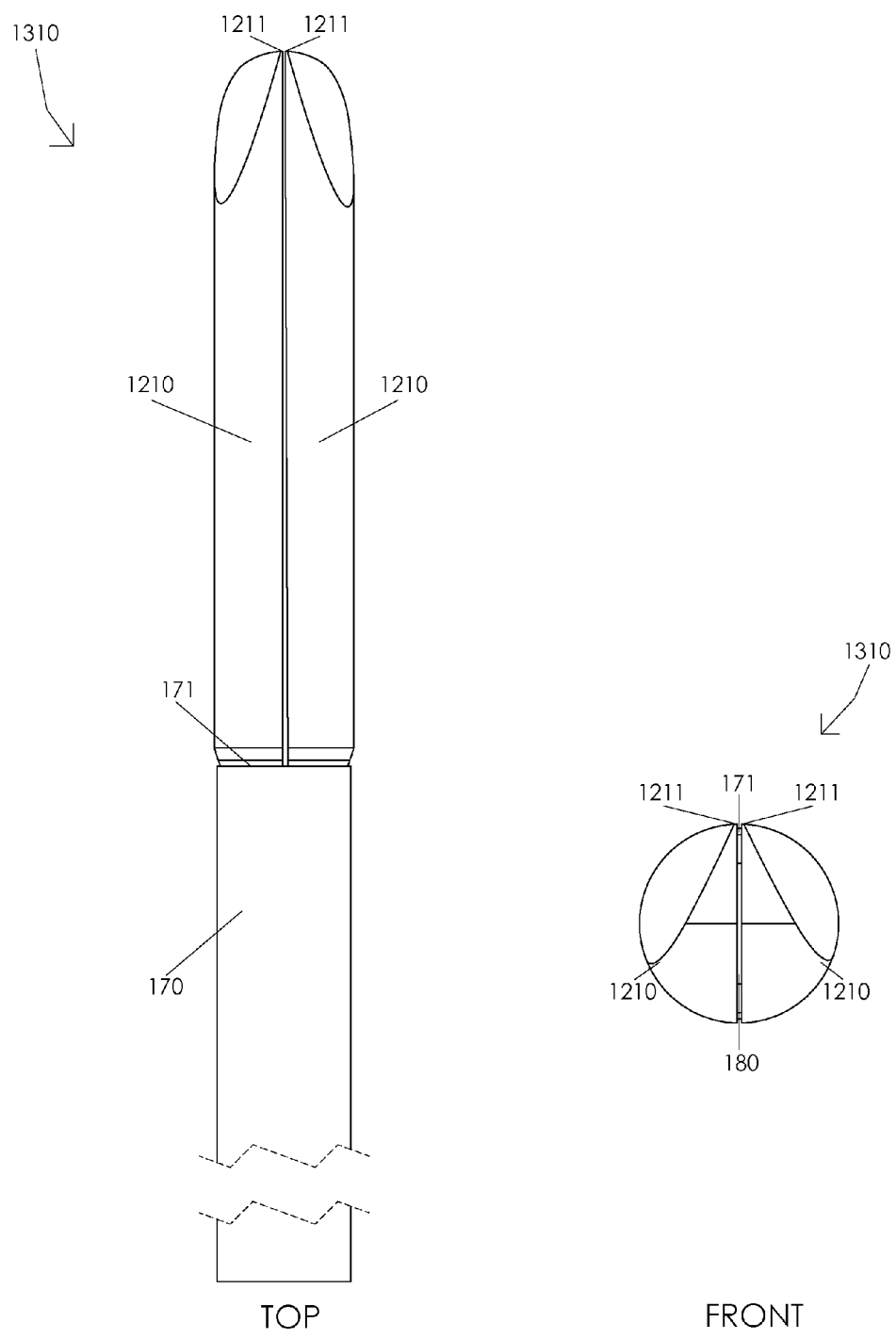
Figure 13C:
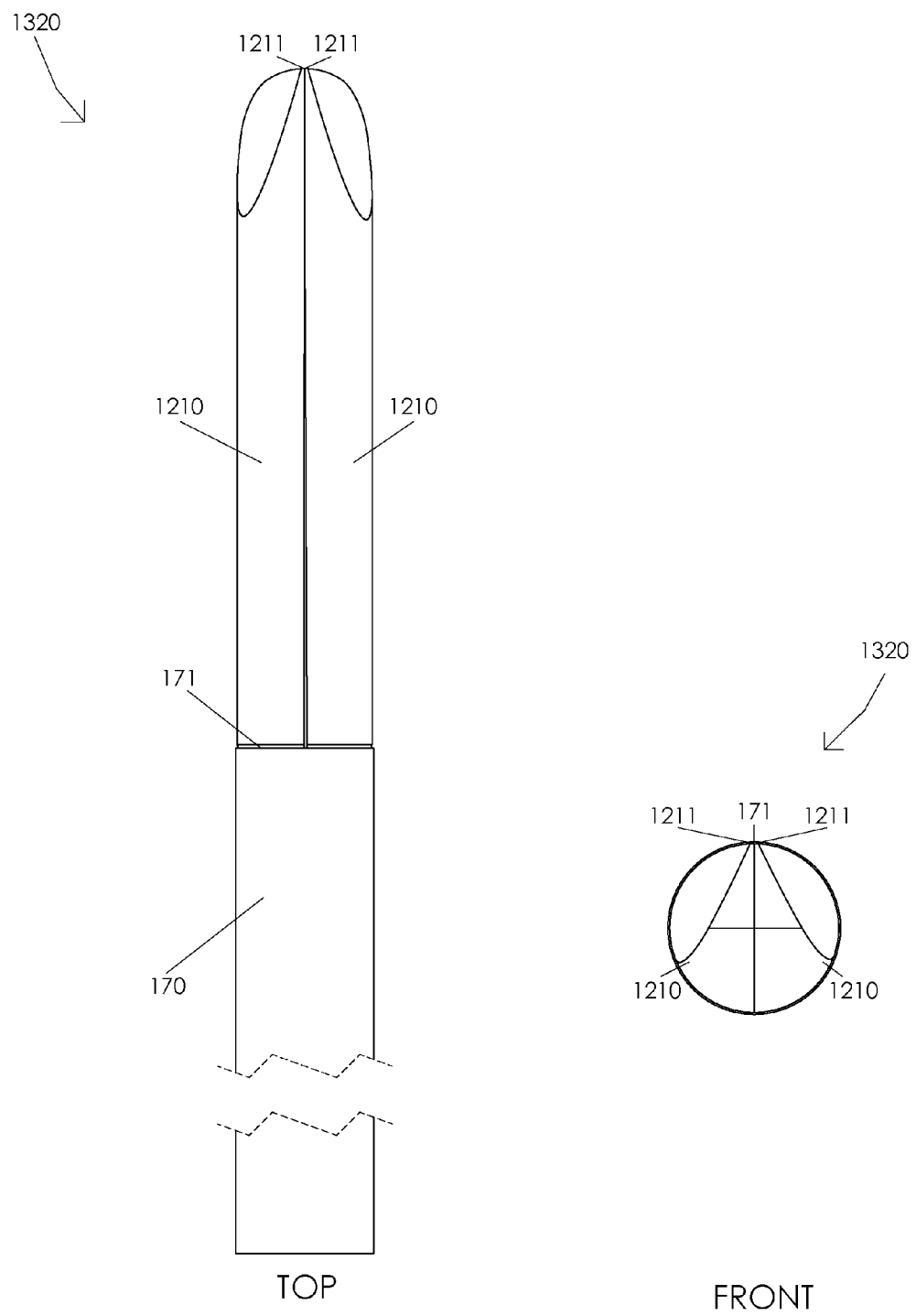

FIGS. 13A, 13B, and 13C are schematic diagrams illustrating a gradual closing of an atraumatic forceps 1200. FIG. 13A illustrates a top view and a front view of an open atraumatic forceps 1300. In one or more embodiments, atraumatic forceps 1200 may comprise an open atraumatic forceps 1300, e.g., when a first atraumatic forceps jaw distal end 1211 is separated from a second atraumatic forceps jaw distal end 1211 by distance 1215. Illustratively, atraumatic forceps 1200 may comprise an open atraumatic forceps 1300, e.g., when outer hypodermic tube 170 is fully retracted relative to atraumatic forceps jaws proximal ends 1212. Illustratively, atraumatic forceps 1200 may comprise an open atraumatic forceps 1300, e.g., when handle 110 is fully decompressed.

FIG. 13B illustrates a top view and a front view of a partially closed atraumatic forceps 1310. In one or more embodiments, a compression of handle 110 may be configured to gradually close an atraumatic forceps 1200, e.g., from an open atraumatic forceps 1300 to a partially closed atraumatic forceps 1310. Illustratively, a compression of handle 110 may be configured to extend outer hypodermic tube 170 relative to surgical blank 180, e.g., a compression of handle 110 may be configured to extend outer hypodermic tube distal end 171 over atraumatic forceps jaws proximal ends 1212. In one or more embodiments, a compression of handle 110 may be configured to decrease a distance between a first atraumatic forceps jaw distal end 1211 and a second atraumatic forceps jaw distal end 1211, e.g., a first atraumatic forceps jaw distal end 1211 and a second atraumatic forceps jaw distal end 1211 may be separated by a distance less than distance 1215 when atraumatic forceps 1200 comprises a partially closed atraumatic forceps 1310.

FIG. 13C illustrates a top view and a front view of a fully closed atraumatic forceps 1320. Illustratively, a compression of handle 110 may be configured to gradually close an atraumatic forceps 1200, e.g., from a partially closed atraumatic forceps 1310 to a fully closed atraumatic forceps 1320. In one or more embodiments, a compression of handle 110 may be configured to extend outer hypodermic tube 170 relative to surgical blank 180, e.g., a compression of handle 110 may be configured to extend outer hypodermic tube distal end 171 over atraumatic forceps jaws proximal ends 1212. Illustratively, an extension of outer hypodermic tube 170 over atraumatic forceps jaws proximal ends 1212 may be configured to close atraumatic forceps jaws 1210 wherein atraumatic forceps jaws 1210 initially contact at atraumatic forceps jaws distal ends 1211. In one or more embodiments, a compression of handle 110 may be configured to gradually close atraumatic forceps jaws 1210 wherein atraumatic forceps jaws 1210 initially contact at atraumatic forceps jaws distal ends 1211. Illustratively, after atraumatic forceps jaws distal ends 1211 initially contact, a compression of handle 110 may be configured to gradually close atraumatic forceps jaws 1210 wherein a contact area between atraumatic forceps jaws 1210 gradually increases. In one or more embodiments, atraumatic forceps jaws 1210 may be configured to close wherein an amount of a first atraumatic forceps jaw 1210 in contact with a second atraumatic forceps jaw 1210 increases gradually from atraumatic forceps jaws distal ends 1211, e.g., atraumatic forceps jaws 1210 may be configured to close wherein an amount of a first atraumatic forceps jaw 1210 in contact with a second atraumatic forceps jaw 1210 increases gradually towards atraumatic forceps jaws proximal ends 1212. Illustratively, a compression of handle 110 may be configured to close atraumatic forceps jaws 1210 starting at atraumatic forceps jaws distal ends 1211 and gradually progressing towards atraumatic forceps jaws proximal ends 1212. In one or more embodiments, a compression of handle 110 may be configured to close a first atraumatic forceps jaw 1210 and a second atraumatic forceps jaw 1210 wherein the first and second atraumatic forceps jaws 1210 initially contact each other at first and second atraumatic forceps jaws distal ends 1211. Illustratively, after the first and second atraumatic forceps jaws 1210 initially contact at first and second atraumatic forceps jaws distal ends 1211, a compression of handle 110 may be configured to cause medial portions of the first and second atraumatic forceps jaws 1210 to gradually contact each other starting at medial portions of the first and second atraumatic forceps jaws 1210 adjacent to first and second atraumatic forceps jaws distal ends 1211.

In one or more embodiments, a surgeon may separate an internal limiting membrane from a retina by grasping the internal limiting membrane with atraumatic forceps jaws 1210, e.g., without damaging the retina. Illustratively, a surgeon may manipulate handle 110 and assembled surgical instrument 200 to approach a retina with atraumatic forceps 1200, e.g., when atraumatic forceps 1200 comprises an open atraumatic forceps 1300. For example, a surgeon may gradually move atraumatic forceps jaws distal ends 1211 closer to a retina until atraumatic forceps jaws distal ends 1211 contact an internal limiting membrane. In one or more embodiments, a compression of handle 110, e.g., by a surgeon, may be configured to extend outer hypodermic tube 170 over atraumatic forceps jaws proximal ends 1212. Illustratively, a surgeon may grasp an internal limiting membrane with atraumatic forceps jaws distal ends 1211 and no other portion of atraumatic forceps jaws 1210, e.g., to minimize trauma to an underlying retinal tissue. For example, after a surgeon grasps a first portion of an internal limiting membrane with atraumatic forceps jaws distal ends 1211, the surgeon may manipulate the first portion of the internal limiting membrane and compress handle 110 to grasp a second portion of the internal limiting membrane with atraumatic forceps jaws 1210. Illustratively, the surgeon may grasp the second portion of the internal limiting membrane with a portion of atraumatic forceps jaws 1210 located a distance from atraumatic forceps jaws distal ends 1211.

Figure 14A:
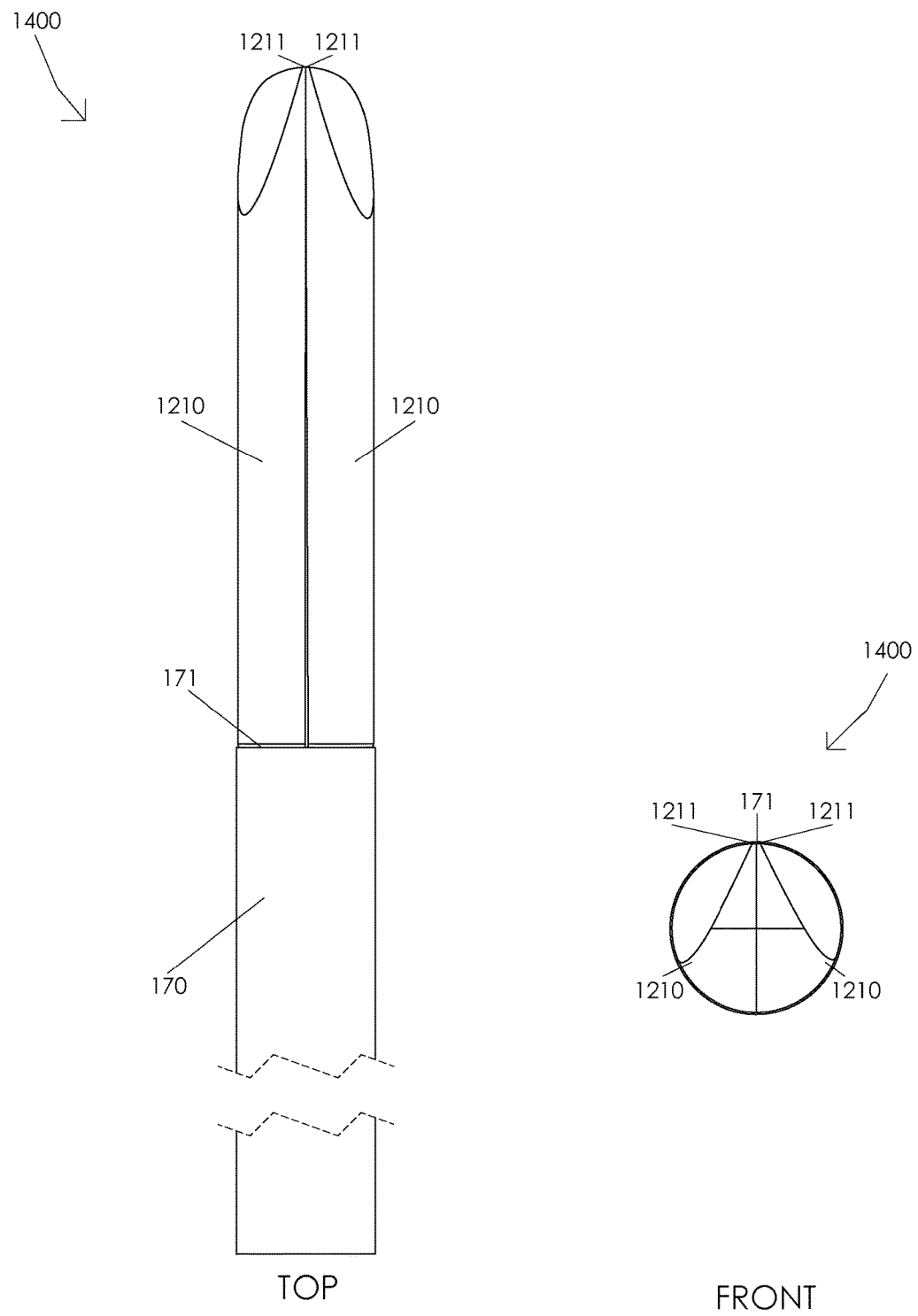
FIGS. 14A, 14B, and 14C are schematic diagrams illustrating a gradual opening of an atraumatic forceps.
Figure 14B:
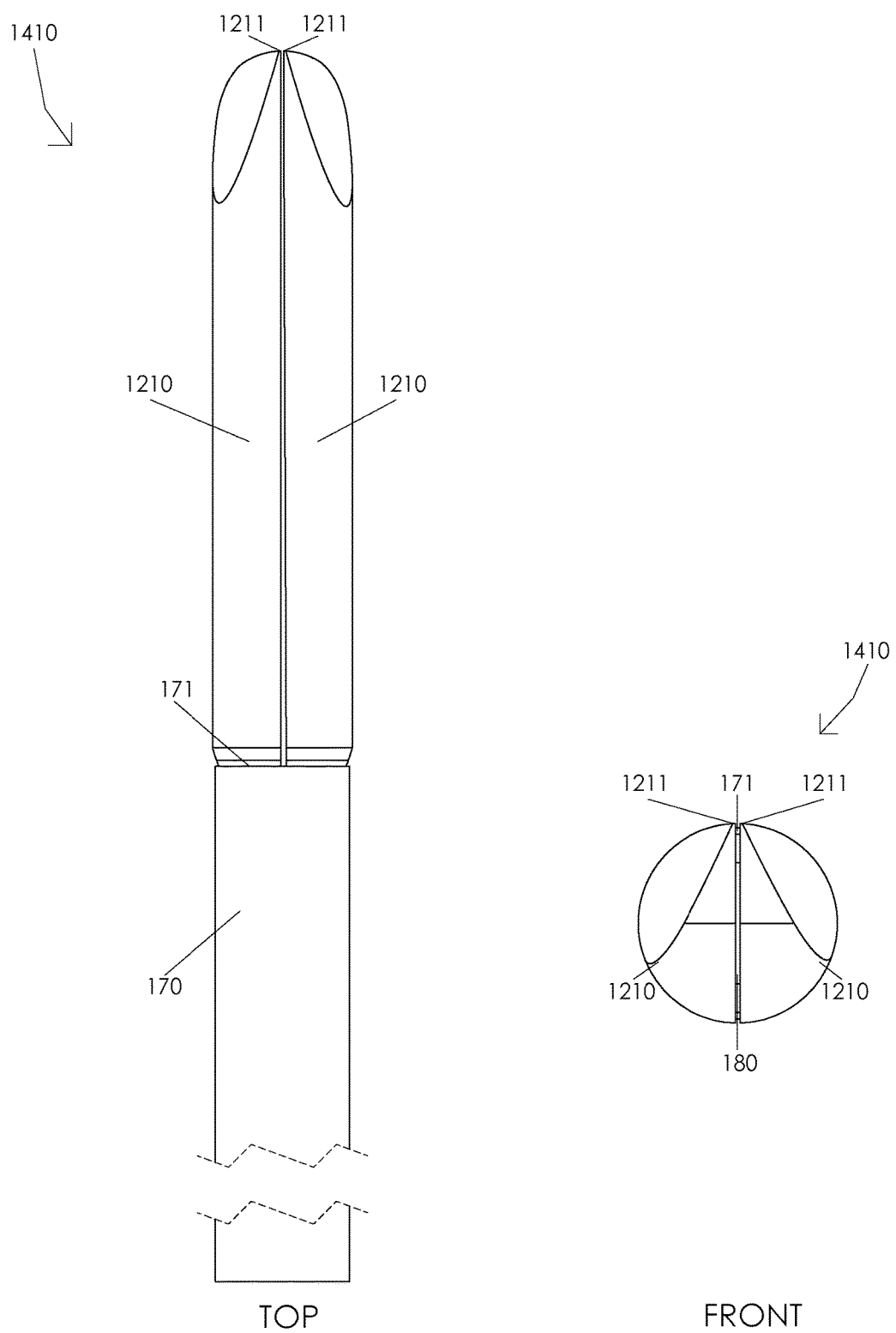
Figure 14C:
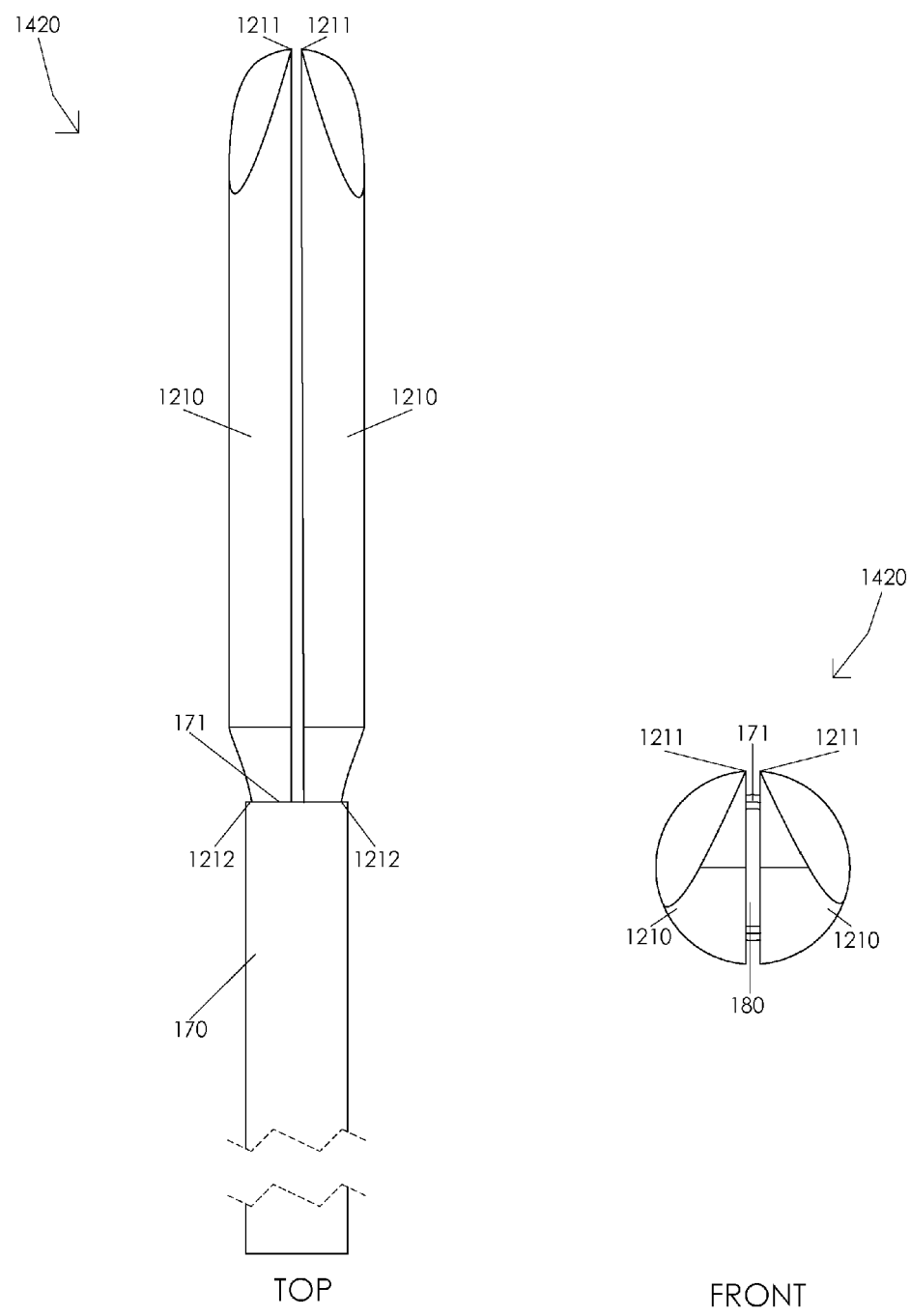

FIGS. 14A, 14B, and 14C are schematic diagrams illustrating a gradual opening of an atraumatic forceps 1200. FIG. 14A illustrates a top view and a front view of a closed atraumatic forceps 1400. In one or more embodiments, atraumatic forceps 1200 may comprise a closed atraumatic forceps 1400, e.g., when a first atraumatic forceps jaw distal end 1211 is adjacent to a second atraumatic forceps jaw distal end 1211. Illustratively, atraumatic forceps 1200 may comprise a closed atraumatic forceps 1400, e.g., when outer hypodermic tube 170 is fully extended over atraumatic forceps jaws proximal ends 1212. Illustratively, atraumatic forceps 1200 may comprise a closed atraumatic forceps 1400, e.g., when handle 110 is fully compressed.

FIG. 14B illustrates a top view and a front view of a partially open atraumatic forceps 1410. In one or more embodiments, a decompression of handle 110 may be configured to gradually open an atraumatic forceps 1200, e.g., from a closed atraumatic forceps 1400 to a partially open atraumatic forceps 1410. Illustratively, a decompression of handle 110 may be configured to retract outer hypodermic tube 170 relative to surgical blank 180, e.g., a decompression of handle 110 may be configured to retract outer hypodermic tube distal end 171 relative to atraumatic forceps jaws proximal ends 1212. In one or more embodiments, a decompression of handle 110 may be configured to gradually separate atraumatic forceps jaws 1210. Illustratively, a decompression of handle 110 may be configured to gradually separate atraumatic forceps jaws 1210 wherein a first atraumatic forceps jaw distal end 1211 contacts a second atraumatic forceps jaw distal end 1211 until all other portions of atraumatic forceps jaws 1210 are separated. In one or more embodiments, a decompression of handle 110 may be configured to separate atraumatic forceps jaws 1210 wherein atraumatic forceps jaws distal ends 1211 are the last portions of atraumatic forceps jaws 1210 to separate.

FIG. 14C illustrates a top view and a front view of a fully open atraumatic forceps 1420. Illustratively, a decompression of handle 110 may be configured to gradually open an atraumatic forceps 1200, e.g., from a partially open atraumatic forceps 1410 to a fully open atraumatic forceps 1420. In one or more embodiments, a decompression of handle 110 may be configured to retract outer hypodermic tube 170 relative to surgical blank 180, e.g., a decompression of handle 110 may be configured to retract outer hypodermic tube distal end 171 relative to atraumatic forceps jaws proximal ends 1212. Illustratively, a decompression of handle 110 may be configured to gradually separate atraumatic forceps jaws 1210. In one or more embodiments, a first atraumatic forceps jaw distal end 1211 and a second atraumatic forceps jaw distal end 1211 may be separated by distance 1215, e.g., when atraumatic forceps 1200 comprises a fully open atraumatic forceps 1420.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any system. Furthermore, while this description has been written in terms of a surgical instrument, the teachings of the present invention are equally suitable to any systems where the functionality may be employed. Therefore, it is the object of the appended claims to cover all such variations and modifications as come within the true spirit and scope of the invention.

What is claimed is:

1. An instrument comprising
a handle having a handle distal end and a handle proximal end;
a surgical blank having a surgical blank distal end and a surgical blank proximal end, at least a portion of the surgical blank disposed in the handle;
an end plug having an end plug distal end and an end plug proximal end wherein at least a portion of the end plug is disposed in the handle;
a Luer taper of the end plug;
a housing sleeve having a housing sleeve distal end and a housing sleeve proximal end, the housing sleeve disposed in the handle;
an actuation facilitating sleeve having an actuation facilitating sleeve distal end and an actuation facilitating sleeve proximal end, the actuation facilitating sleeve at least partially disposed in the housing sleeve;
a piston tube having a piston tube distal end and a piston tube proximal end, the piston tube at least partially disposed in the actuation facilitating sleeve;
an inner hypodermic tube having an inner hypodermic tube distal end and an inner hypodermic tube proximal end, the inner hypodermic tube at least partially disposed in the piston tube;
a front plug wherein at least a portion of the front plug is disposed in the housing sleeve and the actuation facilitating sleeve;
a distal O-ring, the distal O-ring disposed over a portion of the front plug wherein the distal O-ring is disposed in the housing sleeve and the actuation facilitating sleeve;
a first atraumatic forceps jaw of the surgical blank having a first atraumatic forceps jaw distal end and a first atraumatic forceps jaw proximal end;
a second atraumatic forceps jaw of the surgical blank having a second atraumatic forceps jaw distal end and a second atraumatic forceps jaw proximal end; and
an outer hypodermic tube having an outer hypodermic tube distal end and an outer hypodermic tube proximal end, the outer hypodermic tube disposed over the surgical blank wherein a compression of the handle is configured to close the first and second atraumatic forceps jaws wherein the first and second atraumatic forceps jaws initially contact at the first and second atraumatic forceps jaws distal ends.

2. The instrument of claim 1 further comprising:
a first contour angle of the first atraumatic forceps jaw, the first contour angle of the first atraumatic forceps jaw in a range of 60 to 80 degrees; and
a first contour angle of the second atraumatic forceps jaw, the first contour angle of the second atraumatic forceps jaw in a range of 60 to 80 degrees.

3. The instrument of claim 2 further comprising:
a second contour angle of the first atraumatic forceps jaw, the second contour angle of the first atraumatic forceps jaw in a range of 100 to 120 degrees; and
a second contour angle of the second atraumatic forceps jaw, the second contour angle of the second atraumatic forceps jaw in a range of 100 to 120 degrees.

4. The instrument of claim 3 further comprising:
a third contour angle of the first atraumatic forceps jaw, the third contour angle of the first atraumatic forceps jaw in a range of 160 to 175 degrees; and
a third contour angle of the second atraumatic forceps jaw, the third contour angle of the second atraumatic forceps jaw in a range of 160 to 175 degrees.

5. The instrument of claim 1 wherein the first atraumatic forceps jaw distal end and the second atraumatic forceps jaw distal end are separated by a distance in a range of 0.005 to 0.08 inches.

6. The instrument of claim 5 wherein the first atraumatic forceps jaw distal end and the second atraumatic forceps jaw distal end are separated by a distance of 0.04 inches.

7. The instrument of claim 1 wherein the first atraumatic forceps jaw distal end and the second atraumatic forceps jaw distal end are separated by a distance in a range of 200 to 600 times an average thickness of an internal limiting membrane tissue.

8. The instrument of claim 1 wherein at least a portion of the actuation facilitating sleeve comprises glass.

9. The instrument of claim 1 wherein at least a portion of the actuating facilitating sleeve comprises graphite.

10. The instrument of claim 1 wherein at least a portion of the piston tube comprises glass.

11. The instrument of claim 1 wherein at least a portion of the piston tube comprises graphite.

12. The instrument of claim 1 further comprising:
a nosecone having a nosecone distal end and a nosecone proximal end wherein the outer hypodermic tube is disposed in the nosecone.

13. The instrument of claim 12 further comprising:
a first link.

14. The instrument of claim 13 further comprising:
a first link pin, the first link pin disposed in the first link and the handle.

15. The instrument of claim 14 further comprising:
a second link pin, the second link pin disposed in the first link and the nosecone.

16. The instrument of claim 15 further comprising:
a second link.

17. The instrument of claim 1 wherein at least a portion of the actuation facilitating sleeve comprises a non-crystalline material.

18. The instrument of claim 1 wherein at least a portion of the actuation facilitating sleeve comprises a carbon allotrope.

19. The instrument of claim 1 wherein at least a portion of the piston tube comprises a non-crystalline material.

20. The instrument of claim 1 wherein at least a portion of the piston tube comprises a carbon allotrope.

* * * * *